United States Patent
Ruben

(10) Patent No.: US 11,950,387 B2
(45) Date of Patent: Apr. 2, 2024

(54) METHODS FOR FORMING HERMETICALLY-SEALED PACKAGES INCLUDING FEEDTHROUGH ASSEMBLIES

(71) Applicant: Medtronic, Inc., Minneapolis, MN (US)

(72) Inventor: David A. Ruben, Mesa, AZ (US)

(73) Assignee: Medtronic, Inc., Minneapolis, MN (US)

( * ) Notice: Subject to any disclaimer, the term of this patent is extended or adjusted under 35 U.S.C. 154(b) by 501 days.

(21) Appl. No.: 17/074,171

(22) Filed: Oct. 19, 2020

(65) Prior Publication Data

US 2021/0051812 A1 Feb. 18, 2021

Related U.S. Application Data

(63) Continuation of application No. 16/192,933, filed on Nov. 16, 2018, now Pat. No. 10,813,238, which is a
(Continued)

(51) Int. Cl.
*H05K 5/06* (2006.01)
*A61N 1/375* (2006.01)
(Continued)

(52) U.S. Cl.
CPC ........... *H05K 5/066* (2013.01); *A61N 1/3754* (2013.01); *H05K 3/38* (2013.01); *H05K 5/06* (2013.01);
(Continued)

(58) Field of Classification Search
CPC .......... A61N 1/3754; H05K 3/38; H05K 5/06; H05K 5/066; H05K 7/06; H05K 2203/107
See application file for complete search history.

(56) References Cited

U.S. PATENT DOCUMENTS

| 4,605,007 A | 8/1986 | Heraly |
| 4,700,473 A | 10/1987 | Freyman |

(Continued)

FOREIGN PATENT DOCUMENTS

| CN | 102824692 | 12/2012 |
| CN | 2910251 | 2/2013 |

(Continued)

OTHER PUBLICATIONS

Office Action dated Nov. 6, 2020 from Chinese Patent Application No. 201580071078.5, 9 pages.
(Continued)

*Primary Examiner* — Jeffrey T Carley
*Assistant Examiner* — Jose K Abraham
(74) *Attorney, Agent, or Firm* — Mueting Raasch Group

(57) ABSTRACT

Methods of forming hermetically-sealed packages are disclosed. In one or more embodiments, the hermetically-sealed package can include a housing and a feedthrough assembly that forms a part of the housing. The feedthrough assembly can include a non-conductive substrate and a feedthrough. The feedthrough can include a via from an outer surface to an inner surface of the non-conductive substrate, a conductive material disposed in the via, and an external contact disposed over the via on the outer surface of the non-conductive substrate. The external contact can be electrically coupled to the conductive material disposed in the via. Further, the external contact can be hermetically sealed to the outer surface of the non-conductive substrate by a laser bond surrounding the via.

20 Claims, 14 Drawing Sheets

Related U.S. Application Data continuation of application No. 14/966,181, filed on Dec. 11, 2015, now Pat. No. 10,136,535.

(60) Provisional application No. 62/096,699, filed on Dec. 24, 2014.

(51) Int. Cl.
  *H05K 3/38* (2006.01)
  *H05K 7/06* (2006.01)

(52) U.S. Cl.
  CPC ......... *H05K 7/06* (2013.01); *H05K 2203/107* (2013.01)

(56) References Cited

U.S. PATENT DOCUMENTS

| | | | |
|---|---|---|---|
| 4,785,827 A | 11/1988 | Fischer | |
| 4,810,318 A | 3/1989 | Haisma | |
| 5,054,683 A | 10/1991 | Haisma | |
| 5,315,486 A * | 5/1994 | Fillion | H01L 23/13 257/676 |
| 5,489,321 A | 2/1996 | Tracy | |
| 5,569,243 A * | 10/1996 | Kortenbach | A61B 18/1445 606/174 |
| 5,647,932 A | 7/1997 | Taguchi | |
| 5,693,111 A | 12/1997 | Kadowaki | |
| 5,814,091 A | 9/1998 | Dahlberg | |
| 6,071,597 A | 6/2000 | Yang et al. | |
| 6,459,566 B1 | 10/2002 | Casby et al. | |
| 6,477,901 B1 | 11/2002 | Tadigadapa | |
| 6,555,025 B1 | 4/2003 | Krupetsky | |
| 6,717,100 B2 | 4/2004 | Ruben | |
| 6,762,072 B2 | 7/2004 | Lutz | |
| 6,822,326 B2 | 11/2004 | Enquist | |
| 6,963,780 B2 | 11/2005 | Ruben | |
| 7,078,726 B2 | 7/2006 | Pichler | |
| 7,136,273 B2 * | 11/2006 | Stevenson | H01G 4/35 333/182 |
| 7,145,076 B2 * | 12/2006 | Knappen | H01G 4/35 174/50.56 |
| 7,153,775 B2 | 12/2006 | Geusic | |
| 7,288,847 B2 | 10/2007 | Ruben | |
| 7,417,307 B2 | 8/2008 | Haluzak | |
| 7,540,934 B2 | 6/2009 | Hofmann | |
| 7,623,335 B2 * | 11/2009 | Stevenson | H01G 4/35 333/182 |
| 7,647,110 B2 | 1/2010 | Hormfeldt | |
| 7,794,866 B2 | 9/2010 | Youker | |
| 7,822,482 B2 | 10/2010 | Gerber | |
| 7,872,208 B2 | 1/2011 | Ruben | |
| 7,902,851 B2 | 3/2011 | Fenner | |
| 8,125,146 B2 | 2/2012 | Park | |
| 8,231,998 B2 | 7/2012 | Sastry | |
| 8,233,986 B2 | 7/2012 | Deininger | |
| 8,295,929 B2 | 10/2012 | Fang | |
| 8,448,468 B2 | 5/2013 | Pastel | |
| 8,473,056 B2 | 6/2013 | Engmark | |
| 8,626,310 B2 | 1/2014 | Barror | |
| 8,644,936 B2 | 2/2014 | Iyer | |
| 8,648,265 B2 * | 2/2014 | Talamine | A61N 1/3754 174/650 |
| 8,666,505 B2 | 3/2014 | O'Brien | |
| 8,796,109 B2 | 8/2014 | Ruben | |
| 8,941,020 B2 * | 1/2015 | Pretzlaff | H01M 50/176 174/650 |
| 9,120,287 B2 | 9/2015 | Ruben | |
| 9,171,121 B2 | 10/2015 | Ding | |
| 9,889,306 B2 * | 2/2018 | Stevenson | H01G 2/103 |
| 9,968,794 B2 * | 5/2018 | Ruben | H05K 3/42 |
| 2002/0066940 A1 | 6/2002 | Ruben | |
| 2002/0115920 A1 | 8/2002 | Rich | |
| 2003/0018364 A1 | 1/2003 | Belden | |
| 2003/0179536 A1 * | 9/2003 | Stevenson | H01G 4/35 361/302 |
| 2004/0012083 A1 | 1/2004 | Farrell | |
| 2004/0056350 A1 | 3/2004 | Ruben | |
| 2004/0082145 A1 | 4/2004 | Reichenbach | |
| 2005/0007718 A1 | 1/2005 | Stevenson | |
| 2005/0151151 A1 | 7/2005 | Hawtof | |
| 2005/0284815 A1 | 12/2005 | Sparks | |
| 2006/0028784 A1 * | 2/2006 | Brendel | H01G 4/35 361/302 |
| 2006/0085043 A1 * | 4/2006 | Stevenson | H01G 4/232 607/36 |
| 2006/0170110 A1 | 8/2006 | Akram et al. | |
| 2006/0247714 A1 | 11/2006 | Taylor | |
| 2006/0259093 A1 * | 11/2006 | Stevenson | A61N 1/3754 607/36 |
| 2006/0267167 A1 | 11/2006 | McCain | |
| 2007/0043399 A1 | 2/2007 | Stevenson | |
| 2007/0160748 A1 | 7/2007 | Schugt | |
| 2007/0170839 A1 | 7/2007 | Choi | |
| 2008/0102096 A1 | 5/2008 | Molin | |
| 2008/0140148 A1 | 6/2008 | Rogier | |
| 2008/0161886 A1 * | 7/2008 | Stevenson | A61N 1/3754 333/176 |
| 2008/0183225 A1 | 7/2008 | Adamski | |
| 2008/0265423 A1 | 10/2008 | Ruben | |
| 2008/0269623 A1 | 10/2008 | Ruben | |
| 2009/0059468 A1 | 3/2009 | Iyer | |
| 2009/0308169 A1 | 12/2009 | Mothilal | |
| 2010/0009150 A1 | 1/2010 | Mitooka | |
| 2010/0262208 A1 | 10/2010 | Parker | |
| 2010/0263794 A1 | 10/2010 | George | |
| 2010/0304151 A1 | 12/2010 | Tuennermann | |
| 2010/0314149 A1 | 12/2010 | Gerrish | |
| 2011/0190833 A1 | 8/2011 | Ries | |
| 2011/0270099 A1 | 11/2011 | Ruben | |
| 2012/0100318 A1 | 4/2012 | Danzl | |
| 2012/0101540 A1 | 4/2012 | O'Brien | |
| 2012/0108954 A1 | 5/2012 | Schulhauser | |
| 2012/0197155 A1 | 8/2012 | Mattes | |
| 2012/0303105 A1 | 11/2012 | Askarinya | |
| 2012/0309237 A1 | 12/2012 | Marzano | |
| 2013/0035733 A1 | 2/2013 | Breyen | |
| 2013/0096661 A1 | 4/2013 | Greenberg et al. | |
| 2013/0184797 A1 * | 7/2013 | Tang | A61N 1/08 607/116 |
| 2013/0196214 A1 | 8/2013 | Scott | |
| 2013/0337313 A1 | 12/2013 | Askarinya | |
| 2014/0194964 A1 * | 7/2014 | Woods | H01R 13/7195 607/119 |
| 2014/0262493 A1 * | 9/2014 | Markham | B23K 26/206 174/650 |
| 2015/0101841 A1 | 4/2015 | Ruben | |
| 2015/0116053 A1 * | 4/2015 | Stevenson | A61N 1/3754 333/176 |
| 2015/0250386 A1 | 9/2015 | Jose James | |
| 2016/0184593 A1 | 6/2016 | Ruben | |
| 2016/0185081 A1 | 6/2016 | Sandlin | |
| 2016/0190052 A1 | 6/2016 | Ruben | |
| 2016/0190062 A1 | 6/2016 | Zheng et al. | |
| 2016/0192524 A1 | 6/2016 | Ruben | |
| 2017/0172505 A1 | 6/2017 | Ruben | |

FOREIGN PATENT DOCUMENTS

| | | |
|---|---|---|
| CN | 103764221 A | 4/2014 |
| EP | 0232935 A1 | 8/1987 |
| EP | 1864784 A1 | 12/2007 |
| EP | 2617461 A1 | 7/2013 |
| WO | WO0065682 A1 | 11/2000 |
| WO | WO10117382 A1 | 10/2010 |
| WO | 2012087369 A1 | 6/2012 |
| WO | 2012174300 A2 | 12/2012 |
| WO | 2013033062 A2 | 3/2013 |
| WO | 2014049089 A1 | 4/2014 |
| WO | WO16106269 A1 | 6/2016 |
| WO | WO16106272 A1 | 6/2016 |

(56) References Cited

FOREIGN PATENT DOCUMENTS

WO   WO16106274 A1   6/2016
WO   WO16106323 A1   6/2016

OTHER PUBLICATIONS

Office Action dated Nov. 6, 2020 from Chinese Patent Application No. 201580071083.6, 9 pages.
Office Action from EP Application No. 15831104.3 dated Apr. 8, 2021, 4 pages.
Ruben et al., "Feedthrough Assemblies and Methods of Forming Same", Chinese Patent Application No. 201580071078.5, First Office Action Dispatched Nov. 5, 2019, 8 pages.
Ruben, "Hermetically-Sealed Packages Including Feedthrough Assemblies", Chinese Patent Application No. 201580071083.6, First Office Action Dispatched Dec. 3, 2019, 8 pages.
Brown, "Precision Laser Welding of Clear Thermoplastics Without Additives," Medical Design Technology, Aug. 5, 2013, 7 pages. Located on the World Wide Web at http://www.mdtmag.com/articles/2013/08/precision-laser-welding-clear-thermoplastics-without-additives.
Gillner et al., "Laser Bonding of Micro Optical Components," Proceedings of SPIE, vol. 4941, pp. 112-120, Oct. 2003.
International Preliminary Report on Patentability for corresponding patent application No. PCT/US2011/034371, dated Jul. 4, 2013, 7 pages.
International Search Report and Written Opinion of international application No. PCT/US2011/034371, dated Jun. 24, 2011, 11 pp.
Park, "Characterization of transmission laser bonding (TLB) technique for microsystem packaging," Arizona State University, May 2006 (135 pp.).
Sari et al., "Applications of laser transmission processes for the joining of plastics, silicon and glass micro parts," Microsyst Technol (2008) 14: 1879-1886, published online Jul. 18, 2008.
Theppakuttai et al., "Localized Laser Transmission Bonding for Microsystem Fabrication and Packaging," Journal of Manufacturing Processes, vol. 6, No. 1, 2004 (8 pp.).
Wiemer et al., "Developments trends in the field of wafer bonding technologies," 214th ECS Meeting, Abstract #2229, Oct. 12-Oct. 17, 2008, Honolulu, HI (1 p.).
Wild et al. "Locally selective bonding of silicon and glass with laser," Sensors and Actuators A: Physical, vol. 93, Issue 1, Aug. 25, 2001, p. 63-69.
Witte et al., "Laser joining of glass with silicon," Proceedings of SPIE, vol. 4637, Jan. 21, 2002, pp. 487-495.
Claims from U.S. Appl. No. 14/966,181, filed Dec. 11, 2015.
Claims from U.S. Appl. No. 14/966,101, filed Dec. 11, 2015.
(PCT/US2015/067262) PCT Notification of Transmittal of the International Search Report and the Written Opinion of the International Searching Authority, dated Apr. 14, 2016, 11 pages.
(PCT/US2015/067260) PCT Notification of Transmittal of the International Search Report and the Written Opinion of the International Searching Authority, dated Apr. 19, 2016, 10 pages.
(PCT/US15/067257) PCT Notification of Transmittal of the International Search Report and the Written Opinion of the International Searching Authority, dated Mar. 17, 2016, 10 pages.
(PCT/US2016/063859) PCT Notification of Transmittal of the International Search Report and the Written Opinion of the International Searching Authority, dated Feb. 20, 2017, 10 pages.

* cited by examiner

METHODS FOR FORMING HERMETICALLY-SEALED PACKAGES INCLUDING FEEDTHROUGH ASSEMBLIES

CROSS-REFERENCE TO RELATED APPLICATIONS

This application is a continuation of U.S. patent application Ser. No. 16/192,933, filed Nov. 16, 2018, which is a continuation of U.S. patent application Ser. No. 14/966,181, filed Dec. 11, 2015, now U.S. Pat. No. 10,136,535, which claims the benefit of the filing date of Provisional U.S. Application No. 62/096,699, filed on Dec. 24, 2014, the content of both of which is incorporated by reference in their entirety.

BACKGROUND

Various systems require electrical coupling between electrical devices disposed within a hermetically sealed enclosure and external devices. Oftentimes, such electrical coupling needs to withstand various environmental factors such that a conductive pathway or pathways from the external surface to within the enclosure remains stable. For example, implantable medical devices (IMDs), e.g., cardiac pacemakers, defibrillators, neurostimulators and drug pumps, which include electronic circuitry and battery elements, require an enclosure or housing to contain and hermetically seal these elements within a body of a patient. Many of these IMDs include one or more electrical feedthrough assemblies to provide electrical connection between the elements contained within the housing and components of the IMD external to the housing, for example, sensors and/or electrodes and/or lead wires mounted on an exterior surface of the housing, or electrical contacts housed within a connector header, which is mounted on the housing to provide coupling for one or more implantable leads, which typically carry one or more electrodes and/or one or more other types of physiological sensors. A physiological sensor, for example a pressure sensor, incorporated within a body of a lead may also require a hermetically sealed housing to contain electronic circuitry of the sensor and an electrical feedthrough assembly to provide electrical connection between one or more lead wires, which extend within the implantable lead body, and the contained circuitry.

A feedthrough assembly typically includes one or more feedthrough pins that extend from an interior to an exterior of the housing through a ferrule. Each feedthrough pin is electrically isolated from the ferrule, and, for multipolar assemblies, from one another, by an insulator element, e.g., glass or ceramic, that is mounted within the ferrule and surrounds the feedthrough pin(s). Glass insulators are typically sealed directly to the pin(s) and to the ferrule, e.g., by heating the assembly to a temperature at which the glass wets the pin(s) and ferrule, while ceramic insulators are typically sealed to the pin(s) and to the ferrule by a braze joint. High temperatures are typically required to join corrosion-resistant conductive materials with corrosion-resistant insulative materials.

SUMMARY

In general, the present disclosure provides various embodiments of a hermetically-sealed package that includes a feedthrough assembly. In one or more embodiments, the feedthrough assembly can include a substrate and one or more feedthroughs. In one or more embodiments, a feedthrough can include an external contact disposed over a via that is formed from an outer surface to an inner surface of the substrate. The external contact can be hermetically sealed to the outer surface of the substrate by a bond that surrounds the via.

In one aspect, the present disclosure provides a hermetically-sealed package that includes a housing and a feedthrough assembly that forms a part of the housing. The feedthrough assembly includes a non-conductive substrate and a feedthrough. The feedthrough includes a via from an outer surface to an inner surface of the non-conductive substrate, a conductive material disposed in the via, and an external contact disposed over the via on the outer surface of the non-conductive substrate. The external contact is electrically coupled to the conductive material disposed in the via. Further, the external contact is hermetically sealed to the outer surface of the non-conductive substrate by a laser bond surrounding the via.

In another aspect, the present disclosure provides a method of forming a hermetically-sealed package that includes a housing. The method includes forming a feedthrough assembly that includes a non-conductive substrate, and attaching the feedthrough assembly to the housing by forming a laser bond between the feedthrough assembly and the enclosure that hermetically seals the feedthrough assembly to the enclosure.

In another aspect, the present disclosure provides a hermetically-sealed package that includes a housing and a feedthrough assembly that forms a part of the housing. The feedthrough assembly includes a non-conductive substrate and a feedthrough. The feedthrough includes a via from an outer surface to an inner surface of the non-conductive substrate, a conductive material disposed in the via, and an external contact disposed over the via on the outer surface of the non-conductive substrate. The external contact is electrically coupled to the conductive material disposed in the via. Further, the external contact is hermetically sealed to the outer surface of the non-conductive substrate by a bond line surrounding the via.

These and other aspects of the present disclosure will be apparent from the detailed description below. In no event, however, should the above summaries be construed as limitations on the claimed subject matter, which subject matter is defined solely by the attached claims, as may be amended during prosecution.

BRIEF DESCRIPTION OF THE DRAWINGS

Throughout the specification, reference is made to the appended drawings, where like reference numerals designate like elements, and wherein.

DETAILED DESCRIPTION

Figure 1A:
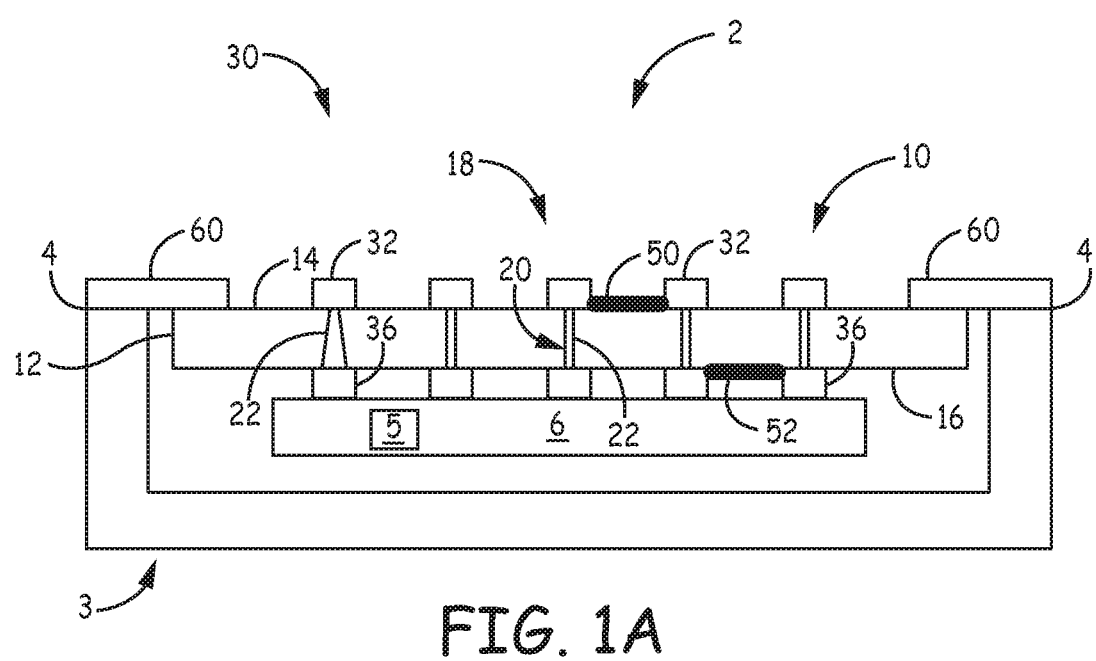
FIG. 1A is a schematic cross-section views of embodiments of hermetically-sealed packages that include a feedthrough assembly.

In general, the present disclosure provides various embodiments of a hermetically-sealed package that includes a feedthrough assembly. In one or more embodiments, the feedthrough assembly can include a substrate and one or more feedthroughs. In one or more embodiments, a feedthrough can include an external contact disposed over a via that is formed from an outer surface to an inner surface of the substrate. The external contact can be hermetically sealed to the outer surface of the substrate by a bond that surrounds the via.

In one or more embodiments, the feedthrough can be formed through the substrate using low temperature techniques that do not require the use of ferrules, glasses, or brazing materials. Further, in one or more embodiments, the feedthrough can be formed without creating unacceptable stresses in the materials used to form the feedthrough that can be caused by the use of high temperature bonding techniques. Further, in one or more embodiments, the external contact of the feedthrough and an optional internal contact electrically coupled to the via can be of sufficient size and thickness to enable laser, resistance, or other welding and joining techniques to be utilized to electrically couple conductors and/or electronic devices to the contacts. In addition, in one or more embodiments, the disclosed low temperature processing techniques can also allow for internal metallization such as Ti/Ni/Au directly on a non-conductive substrate. This can, in one or more embodiments, facilitate the disposition of various electronic devices directly onto the substrate, e.g., integrated circuits, or discrete circuit components such as filtering capacitors, diodes, resistors etc., as will be described in one example below.

The various embodiments of hermetically-sealed packages described herein can be utilized in any suitable application where a conductive pathway is required from an external environment to an electronic device or circuitry disposed within a hermetically-sealed housing or enclosure. In one or more embodiments, the hermetically-sealed package can maintain the integrity of this conductive pathway while protecting enclosed electronic devices or circuitry from undesired external environmental factors.

The various embodiments of hermetically-sealed packages can be utilized with any suitable devices or systems, e.g., electronic systems used, e.g., in smartphones, tablets, laptop computers, construction equipment, underwater equipment, implantable medical devices, etc. For example, implantable medical devices often include a lead that can deliver electrical signals to tissue of a patient and also receive electrical signals from the tissue. Some patient therapies benefit from multiple electrodes on the lead. Typically, the lead includes at least one conductor per electrode running the length of a lead body of the lead. The number of electrodes that can be included with the lead reaches a practical limit based on the conductor size and maximum lead diameter. An alternative approach has been proposed using a multiplexing circuit at or near a distal end of the lead. It can be challenging, however, to protect the multiplexer and associated integrated circuits from the external environment while providing terminals for electrical connections and maintaining a suitably small form factor.

In one or more embodiments, the present disclosure provides a hermetically-sealed package that can provide one or more conductive pathways from an external environment to an electronic device or devices disposed within a housing of the hermetically-sealed package. Further, one or more embodiments of hermetically-sealed packages can be utilized with a lead and a multiplexer to provide electrical pathways to an array of therapeutic electrodes while reducing the number of conductors required within a lead body of the lead.

FIGS. 1A-4 are various schematic views of one embodiment of a hermetically-sealed package 2. The package 2 includes a housing 3 and a feedthrough assembly 10 that can, in one or more embodiments, form a part of the housing. In one or more embodiments, the package 2 can also include one or more electronic devices 6 disposed within the housing 3. The electronic device 6 can be electrically coupled to the feedthrough assembly 10 using any suitable technique or combination of techniques. Although the package 2 is illustrated as including a single feedthrough assembly 10, the package can include any suitable number of feedthrough assemblies attached in any suitable arrangement on the housing 3 or form any part of the housing.

The housing 3 of the package 2 can include any suitable dimensions and take any suitable shape or combination of shapes. In general, the housing 3 is sized and shaped to at least partially surround the electronic device 6. In one or more embodiments, the housing 3 can include one or more sidewalls 4 that can be attached to the feedthrough assembly 10 using any suitable technique or combination of techniques. The housing 3 can completely surround and enclose the electronic device 6, and the feedthrough assembly 10 can be attached to the housing. In one or more embodiments, the housing 3 can include an open side or face, and the feedthrough assembly 10 can be attached to the housing within this open side such that the feedthrough assembly forms a part of the housing. The housing 3 can be a unitary housing or can include one or more sections that are joined together using any suitable technique or combination of techniques.

The housing 3 can include any suitable material or combination of materials, e.g., metal, polymeric, ceramic, or inorganic materials. In one or more embodiments, the housing 3 can include at least one of glass, quartz, silica, sapphire, silicon carbide, diamond, synthetic diamond, and gallium nitride, or alloys or combinations (including clad structures, laminates etc.) thereof. In one or more embodiments, the housing can include at least one of copper, silver, titanium, niobium, zirconium, tantalum, stainless steel, platinum, iridium, or alloys or combinations (including clad structures, laminates etc.) thereof. In one or more embodiments, the housing 3 can include the same material or combination of materials as a substrate 12 of the feedthrough assembly 10.

The package 2 can include any suitable electronic device 6 or electronics that are disposed within the housing 2. In one or more embodiments, the electronic device 6 can include any suitable integrated circuit or circuits, e.g., a controller, a multiplexer, etc. It should be understood that any of the electronic devices mentioned in this disclosure can be coupled to a power source. For instance, in one or more embodiments, the electronic device 6 can also include a power source 5 that is adapted to provide power to one or more integrated circuits or devices disposed within the housing 3 or are exterior to the housing. Any suitable power source 5 can be disposed within the housing, e.g., one or more batteries, capacitors, etc. The power source 5 can be rechargeable by electrically coupling the power source to a power supply through the feedthrough assembly 10. In one or more embodiments, the power source 5 can be adapted to be inductively charged by an inductive power system that is external to the package 2.

The package 2 can include any suitable feedthrough assembly. For example, the embodiment illustrated in FIGS. 1A-4 includes feedthrough assembly 10. The assembly 10 includes a substrate 12 that has an outer surface 14 and an inner surface 16. The assembly 10 also includes one or more feedthroughs 18. In one or more embodiments, the assembly 10 can include an array of feedthroughs 18. The feedthrough assembly 10 can include any suitable number of feedthroughs, e.g., 1, 2, 3, 4, 5, 10, 20, or more feedthroughs. Each feedthrough 18 of the assembly 10 can be substantially identical in construction. In one or more embodiments, one or more feedthroughs can have characteristics that are different from one or more additional feedthroughs. The feedthrough 18 can include a via 20 from the outer surface 14 to the inner surface 16 of the substrate 12. A conductive material 22 can be disposed in the via 20 to provide an electrical pathway from the outer surface 14 to the inner surface 16 of the substrate 12.

Figure 2:
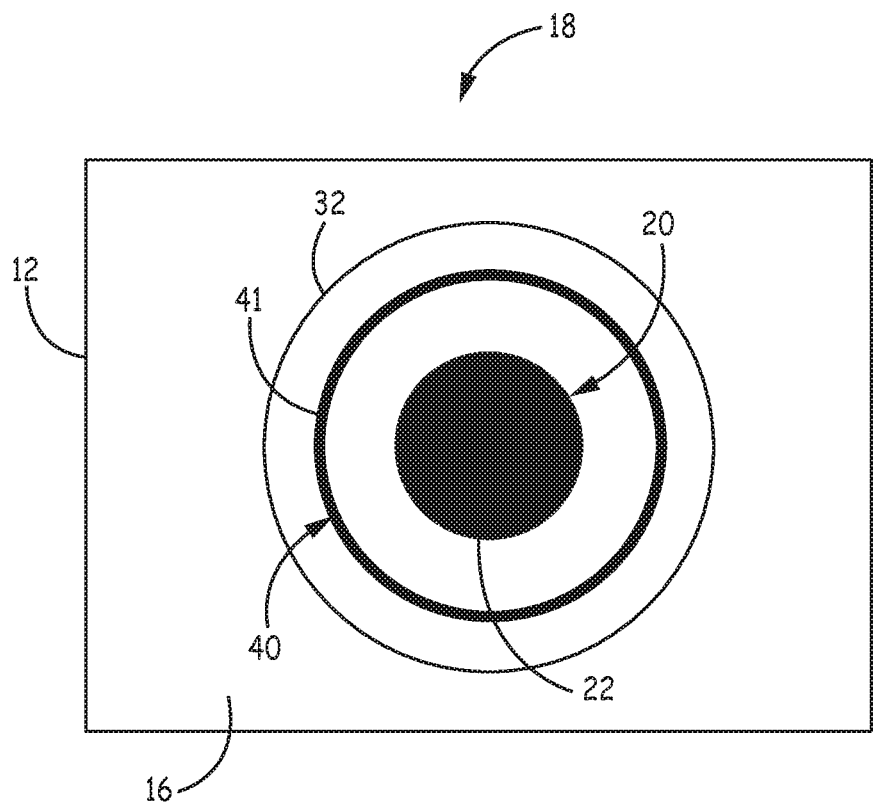
FIG. 2 is a schematic plan view of a feedthrough of the feedthrough assembly of FIGS. 1A AND 1B.
Figure 4:
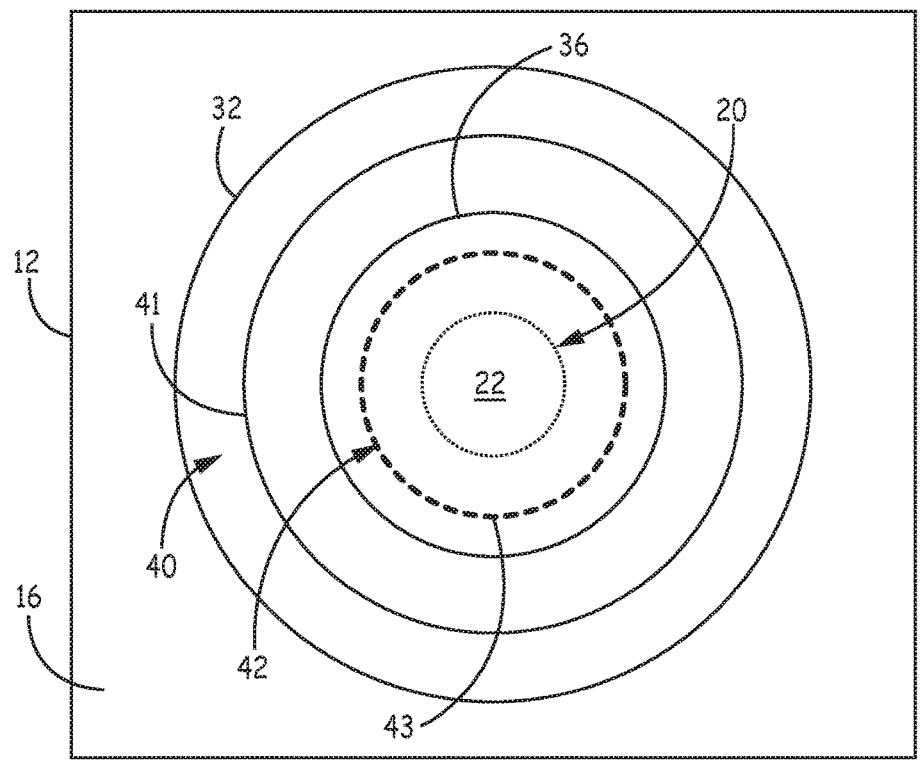
FIG. 4 is a schematic plan view of a feedthrough of the feedthrough assembly of FIGS. 1A AND 1B.

The feedthrough 18 can also include an external contact 32. The external contact 32 can be disposed over the via 20 on the outer surface 14 of the substrate 12. In one or more embodiments, the external contact 32 can be electrically coupled to the conductive material 22 disposed in the via 20. The external contact 32 can be hermetically sealed to the outer surface 14 of the substrate 12, e.g., by a bond 40 that surrounds the via 20 (as shown in FIGS. 2 and 4).

In one or more embodiments, the substrate 12 can be a non-conductive or insulative substrate such that the external contacts 32 and any conductors or other devices disposed on the substrate can be electrically isolated if desired. The substrate 12 can include any suitable material or combination of materials. In one or more embodiments, the substrate 12 can include at least one of glass, quartz, silica, sapphire, silicon carbide, diamond, synthetic diamond, and gallium nitride, or alloys or combinations (including clad structures, laminates etc.) thereof.

Further, in one or more embodiments, the substrate 12 can be substantially transparent at a desired wavelength or range of wavelengths. As used herein, the phrase "substantially transparent" as it pertains to a substrate means that the substrate meets at least one or both of the following minimal energy absorption criteria: (1) the energy transmitted through the substantially transparent substrate material is sufficient to activate the bonding process at the interface via absorption by the opaque material (e.g., interface of substrate 12 and external contact 32), and (2) any energy absorbed by the transparent material will not be sufficient to melt, distort, or otherwise affect the bulk of the transparent material that is away from the bonding region. In other words, the laser bonding techniques described herein will preferentially heat only the outer surface 14 (or an outer layer at the surface 14 of the substrate 12) over the inner bulk of the substrate 12 to create an enhanced bond, such as bond 40. Such a bond may exhibit a relatively greater strength than the bulk strength of the substrate 12. In other words, the light can be configured having any suitable wavelength provided that the substrate 12 will transmit a given percentage of the light that is directed at the substrate 12 to preferentially heat only the outer surface or outer layer instead of the inner bulk to create the enhanced bond. In an embodiment, the light is directed at substrate 12 though outer surface 16 towards the outer surface 14 (or the outer layer at the surface 14 of the substrate 12). In accordance with the foregoing, a substrate that is substantially transparent in one exemplary embodiment will transmit at least 40% of light that is directed at the substrate for a selected wavelength or range of wavelengths, assuming no reflection at the air-substrate boundaries. In accordance with the foregoing, a substantially transparent substrate can be transmissive to light having a wavelength in the range of 1 nm to 30 µm in one or more example embodiments. In other embodiments, a substantially transparent substrate can be selected based on its transmissive properties to light of any desired wavelength. Therefore, a substantially transparent substrate 12 will allow a sufficient amount of light having a predetermined magnitude to be transmitted through the inner bulk of the substrate to the outer surface 14 so as to create the bond 40. In one or more embodiments, the substrate 12 can be substantially transmissive to at least one of UV light, visible light, and IR light. The light can be provided by a laser that has any suitable wavelength or range of wavelengths and any suitable pulse width.

The substrate 12 can include any suitable dimensions, e.g., thicknesses. Further, the substrate 12 can be a single unitary substrate or multiple substrates joined together.

The feedthrough 18 can include the via 20 from the outer surface 14 to the inner surface 16 of the substrate 12. The via 20 can be any suitable size and take any suitable shape. The size and shape of the via 20 is predicated on the thickness of the substrate 12 and the techniques utilized to provide the conductive material that forms the electrical pathway from the outer surface 14 to the inner surface 16 of the substrate 12. Exemplary shapes for the via 20 may include parallel surface walls and/or tapered surface walls as depicted in the figures. In one or more example embodiments where the substrate 12 has a thickness of approximately 100 to 500 µm, a typical opening for the via 20 at the outer surface 14 of the substrate 12 will be no greater than 500 µm, or no greater than 250 µm, or no greater than 100 micrometers, or no greater than 80 micrometers, or no greater than 50 micrometers, or no greater than 10 micrometers. In one or more example embodiments where the substrate 12 has a thickness of approximately 100 to 500 µm, a typical opening for the via 20 at the inner surface 16 of the substrate 12 will have a diameter that is no greater than 500 µm, or no greater than 250 µm, or no greater than 100 micrometers, or no greater than 80 micrometers, or no greater than 50 micrometers, or no greater than 10 micrometers. Of course, the diameter of the via 20 could be larger (or smaller) than the illustrated examples based on the substrate thickness and/or the techniques utilized to provide the conductive material that forms the electrical pathway. Any suitable technique or combination of techniques can be utilized to form the via 20, e.g., drilling, chemical etching, laser etching, etc.

The feedthrough 18 can also include conductive material 22 disposed in the via 20 to provide a conductive pathway from the outer surface 14 to the inner surface 16 of substrate 12. The conductive material 22 can include any suitable conductive material or combination of conductive materials, e.g., copper, titanium, aluminum, chromium, nickel, gold, composites (e.g., silver-filled epoxies), and combinations thereof. The conductive material 22 can be disposed in the via 20 using any suitable technique or combination of techniques to provide a conductive pathway from external contact 32 to one or more devices or contacts disposed on the inner-surface side of the substrate 12. In one or more embodiments, the conductive material 22 can be disposed in the via 20 such that it substantially fills the via. In one or more embodiments, the conductive material can be disposed in the via along sidewalls of the via and the opening of the via at the external surface 14.

The feedthrough 18 can also include the external contact 32. In one or more embodiments, the external contact 32 can be adapted to electrically couple the feedthrough 18 to a conductor or a contact of a device, e.g., a contact of a header of an implantable medical device. Such conductors and contacts can be electrically coupled to the external contact 32 using any suitable technique or combination of techniques, e.g., soldering, physical contact, welding, etc. The external contact 32 can include any suitable conductive material or combination of conductive materials, e.g., copper, silver, titanium, niobium, zirconium, tantalum, stainless steel, platinum, iridium, or alloys or combinations (including clad structures, laminates etc.) thereof. In one or more embodiments, the external contact 32 can include two or more materials, e.g., bi-metals, clad structures or laminates, etc.

Further, the external contact 32 can take any suitable shape or combination of shapes. In one or more embodiments, the external contact 32 can take a circular shape in a plane parallel to the outer surface 14 of the substrate 12. In one or more embodiments, the external contact 32 can take a rectangular shape in the plane parallel to the outer surface 14 of the substrate 12. Further, the external contact 32 can take any suitable shape or combination of shapes in a plane orthogonal to the outer surface 14 of the substrate 12, e.g., square, tapered, domed, etc. In one or more embodiments, the contact 32 can take substantially the same shape as an external contact of one or more additional feedthroughs 18. In one or more embodiments, external contact 32 can take a shape that is different from the shape of an external contact of one or more additional feedthroughs 18. Further, in one or more embodiments, one or more external contacts 32 can include complex shapes such as grooves or channels formed in the contact to facilitate attachment of conductors or electronic devices to the contacts.

The external contact 32 can also include any suitable dimensions. In one or more embodiments, the contact 32 can have any suitable thickness in a direction normal to the outer surface 14 of the substrate 12. It is envisioned that for purposes of this disclosure, the dimension of the substrate thickness is limited only by the fabrication techniques. With that in mind, in one or more example embodiments, a typical thickness can be at least 2 micrometers. In other example embodiments, it may be desirable to have the thickness be less than 10 millimeters, although greater thicknesses are also contemplated in accordance with embodiments of the disclosure. The thickness of the contact 32 can be the same as or different from the thickness of an external contact of one or more additional feedthroughs. In one or more embodiments, the external contact 32 can be of sufficient size and thickness to enable laser, resistance, or other welding and joining techniques to be utilized to electrically couple conductors and/or electronic devices to the external contact.

In one or more embodiments, the external contact 32 can be formed or disposed over the via 20 on the outer surface 14 of the substrate 12. For purposes of the present disclosure, the terms "form," "forming," and "formed" will be used interchangeably with the terms "dispose," "disposing," and "disposed" respectively, such that the terms are considered to be equivalent. In other words, the external contact 32 is disposed over the via 20 such that the contact covers the via and the via is not visible in a plan view of the outer surface 14 of the substrate 12. In one or more embodiments, the external contact 32 (or any of the external contacts described herein) can be formed separate from the substrate 12 as a discrete member, or it could be patterned from a conductive sheet or foil as described below, for example, in FIGS. 7A-E, and disposed over the via 20 by attaching the formed contact to the outer surface 14 of the substrate 12.

The external contact 32 is electrically coupled to the conductive material 22 that is disposed in the via 20. In one or more embodiments, the external contact 32 is in direct contact with the conductive material 22 to electrically couple the contact to the conductive material. In one or more embodiments, one or more additional conductive layers can be disposed between the external contact 32 and the conductive material 22 to electrically couple the external contact to the conductive material.

In one or more embodiments, the external contact 32 is hermetically sealed to the external surface 14 of the substrate 12. Any suitable technique or combination of techniques can be utilized to hermetically seal the external contact 32 to the outer surface 14 of the substrate 12. For example, in one or more embodiments, the external contact 32 can be hermetically sealed to the external surface 14 of the substrate 12 by a bond 40 (FIG. 2) that surrounds the via 20. Any suitable technique or combination of techniques can be utilized to form this bond. For example, in one or more embodiments, the bond 40 can be formed using a laser to provide a laser bond. By surrounding the via 20 with the bond 40 that hermetically seals the external contact 32 to the outer surface 14 of the substrate 12, the via is also protected from the external environment. The electrical coupling between the external contact 32 and the conductive material 22 disposed in the via 20 is, therefore, protected, and the integrity of this electrical pathway from the external surface 14 of the substrate to the internal surface 16 can be maintained. In one or more embodiments, the external contact 32 can also be attached to the outer surface 14 of the substrate 12 using bonds in addition to bond 40. For example, in one or more embodiments, the external contact 32 can be attached to the outer surface 14 by bond 40 and one or more additional bonds between the external contact 32 and the outer surface, e.g., point bonds.

Figure 1B:
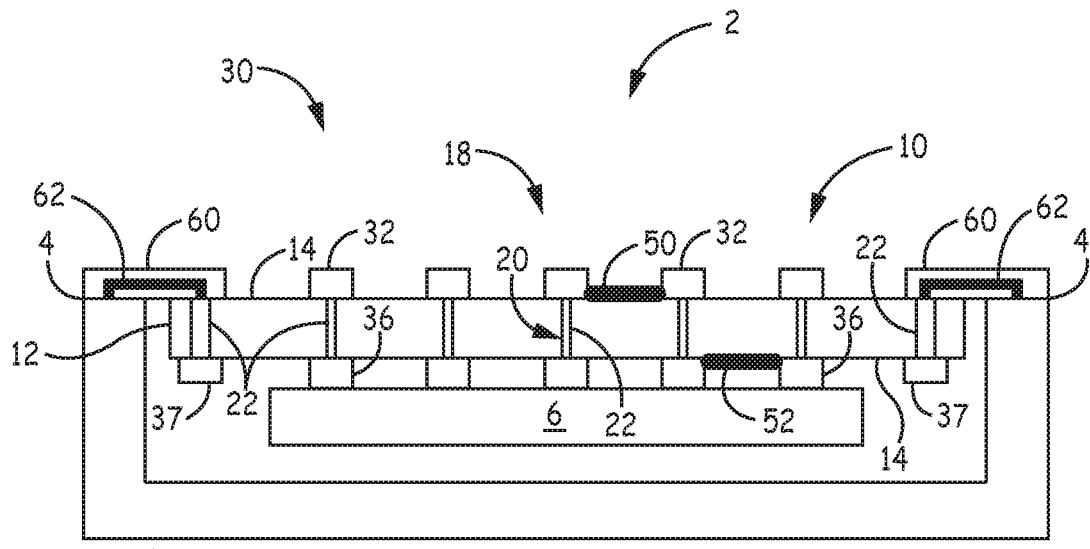
FIG. 1B is a schematic cross-section views of embodiments of hermetically-sealed packages that include a feedthrough assembly.

FIG. 2 is a schematic plan view of a feedthrough 18 of the assembly 10 of FIGS. 1A AND 1B. The feedthrough 18 is shown as viewed through the inner surface 16 of the substrate 12. The feedthrough 18 includes the external contact 32, the via 20 including the conductive material 22 disposed in the via, and the bond 40. The bond 40 hermetically seals the external contact 32 to the outer surface 14 of the substrate 12. The bond 40 can take any suitable shape or combination of shapes such that it surrounds the via 20 as shown in FIG. 2. In one or more embodiments, the bond 40 can be a bond line 41. In one or more embodiments, the bond line 41 can form a closed shape in a plane parallel to the outer surface 14 of the substrate 12. As used herein, the term "closed shape" means that the shape is entirely enclosed such that its perimeter is unbroken and continuous. Any suitable closed shape or shapes can be formed by bond line 41, e.g., elliptical, rectilinear, triangular, polygonal, etc.

In one or more embodiments, the bond 40 can be a bonded region that surrounds the via 20. The bonded region can take any suitable shape or combination of shapes. In one or more embodiments, the bond 40 can include two or more shapes with one shape circumscribing the second shape. For example, the bond 40 can include two or more concentric elliptical bond lines or rings. In such embodiments, the two or more shapes may be isolated so that the shapes do not intersect or overlap. In one or more embodiments, the two or more shapes may intersect or overlap along any suitable portion or portions of the shapes. In one or more embodiments, the bond 40 can include two or more bond lines that together surround the via 20. For example, the bond 40 can include a series of parallel lines that are intersected by two or more lines that are non-parallel to the series of parallel lines.

In one or more embodiments, the bond 40 can include an interfacial layer between the external contact 32 and the substrate 12. It should be understood that the thickness of the interfacial layer, is in part, a function of the desired strength of the bond 40 and the thickness of the external contact 32 and/or the substrate 12. Therefore, this interfacial layer can have any suitable thickness in a direction normal to the outer surface 14 of the substrate 12. In accordance with one or more example embodiments, a typical thickness of the interfacial layer in a direction normal to the outer surface 14 of the substrate 12 includes a thickness of no greater than 10 nm, 100 nm, 150 nm, 200 nm, 500 nm, 1000 nm, or 10 µm.

Figure 3:
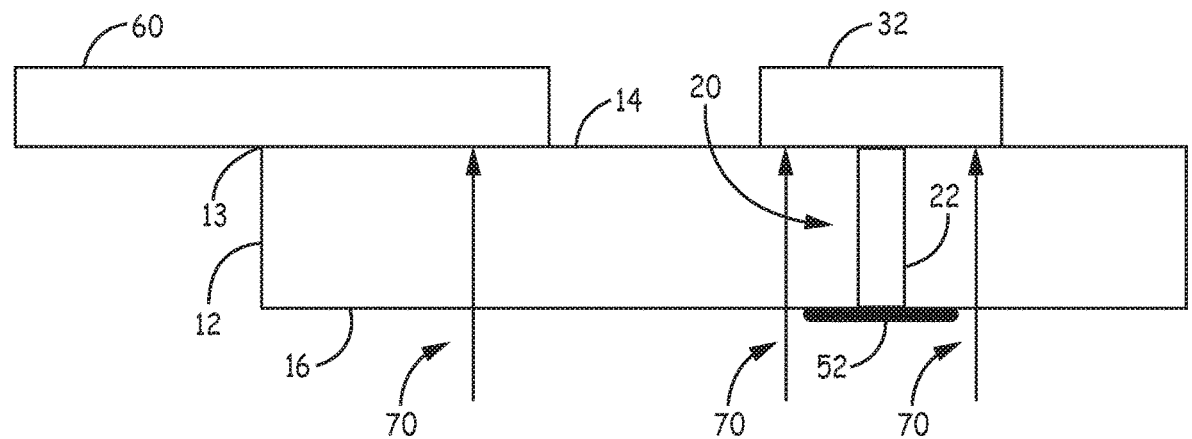
FIG. 3 is a schematic cross-section view of a portion of the feedthrough assembly of FIGS. 1A AND 1B.

As mentioned herein, any suitable technique or combination of techniques can be utilized to form bond 40, e.g., the techniques described in co-owned and co-filed U.S. Patent Application No. 62/096,706 (Medtronic Reference No. C00008775.USP1), entitled KINETICALLY LIMITED NANO-SCALE DIFFUSION BOND STRUCTURES AND METHODS. For example, FIG. 3 is a schematic cross-section view of a portion of the assembly 10 of FIGS. 1A-1B. FIGS. 1A AND 1B. In one or more embodiments, electromagnetic radiation 70 (e.g., light such as laser light) can be directed through substrate 12 from the inner surface 16 and directed (and/or focused) at an interface of the external contact 32 and the outer surface 14 of the substrate. The properties of the electromagnetic radiation 70 can be selected based on the material of the substrate 12 and/or thickness and materials external contact 32 and controlled in a predetermined manner to form the bond. For example, the electromagnetic radiation 70 can include laser light having a suitable wavelength or range of wavelengths and a predetermined pulse width or range of pulse widths in one or more embodiments. The properties of the electromagnetic radiation 70 are predicated on preferentially heating the interface of the substrate 12 and the contact 32 to create an enhanced bond, such as bond 40, having a relatively greater strength than the bulk strength of the substrate 12. Accordingly, a substrate that is substantially transparent may be selected that is transmissive to light of any desired wavelength. For example, laser light 70 can include UV light, visible light, IR light, and combinations thereof. In some exemplary embodiments, some typical lasers utilized to provide laser light 70 have wavelengths in the range of 10 nm to 30 µm and a pulse width in the range of 1 ns to 100 ns. In one or more embodiments, the materials for the substrate 12, the external contact 32, and the power level, pulse width, and wavelength of the light used may be selected such that the light may not directly damage, ablate, warp, or cut the substrate and the contact, and such that the substrate and the contact retain their bulk properties.

In general, light 70 can be provided by any suitable laser or laser system. For example, the laser may generate light having a relatively narrow set of wavelengths (e.g., a single wavelength). In one or more embodiments, the light emitted by the laser may form a collimated beam that may not be focused at a particular point. In one or more embodiments, the light emitted by the laser may be directed and/or focused at a focal point at an interface of the external contact 32 and the outer surface 14 of the substrate 12 to generate a laser bond 40.

Although the laser may provide light 70 that has a narrow range of wavelengths, in one or more embodiments, the laser may represent one or more devices that emit electromagnetic radiation having a wider range of wavelengths than a single typical laser. A wide variety of devices may be used to emit electromagnetic radiation having a narrow or wide range of wavelengths. In one or more embodiments, the laser may include one or more laser devices including diode and fiber lasers. Laser sources may also include, e.g., carbon dioxide lasers, TI sapphire lasers, argon ion lasers, Nd:YAG lasers, XeF lasers, HeNe lasers, Dye lasers, GaAs/AlGaAs lasers, Alexandrite lasers, InGaAs lasers, InGaAsP lasers, Nd:glass lasers, Yb:YAG lasers, and Yb fiber lasers. The laser device may also include one of continuous wave, modulated, or pulsed modes. Accordingly, a wide variety of laser devices may be used in the bonding process. In one or more embodiments, a laser fluence of 1-2 J/cm2 may be used, with a top hat, Gaussian, or other spatial energy profile.

A weld ring 60 can also be attached to the substrate 12. For example, a bond (not shown) can be formed adjacent a perimeter 13 of the substrate 12. Any suitable technique or combination of techniques can be utilized to seal the weld ring 60 to the substrate 12, including for example, the same technique or combination of techniques utilized to attach the external contact 32 to the outer surface 14 of substrate 12. In one or more embodiments, the weld ring 60 can be hermetically sealed to the substrate 12.

The weld ring 60 can take any suitable shape or combination of shapes and include any suitable dimensions. In one or more embodiments, the weld ring 60 surrounds the one or more feedthroughs 18. In general, the weld ring 60 is adapted to attach the assembly 10 to an enclosure, e.g., an enclosure of an implantable medical device. The weld ring 60 can include any suitable material or combination of materials, e.g., the same materials utilized for the external contacts 32.

In one or more embodiments, the feedthrough 18 can include an internal contact 36 disposed on the inner surface 16 of the substrate 12. The internal contact 36 can include any suitable material or combination materials, e.g., the same materials utilized for the external contact 32. Further, the internal contact 36 can take any suitable shape or combination of shapes and have any suitable thickness in a direction normal to the inner surface 16 of the substrate 12, e.g., the same shapes and thicknesses as described regarding the external contact 32.

The internal contact 36 is disposed over the via 20 on the inner surface 16 of the substrate 12. The contact 36 can be electrically coupled to the conductive material 22 disposed in the via 20. The arrangement 30 of the external contact 32, the via 20 and the internal contact 36 facilitates creation of an electrical pathway from the exterior side adjacent to external surface 14 to the interior side adjacent the inner surface 16. In one or more embodiments, the internal contact 36 is hermetically sealed to the inner surface 16 of the substrate 12 using any suitable technique or combination of techniques, e.g., by a bond (e.g., laser bond) that surrounds the via 20. For example, FIG. 4 is a schematic plan view of a portion of the assembly 10 of FIGS. 1A AND 1B. In FIG. 4, the internal contact 36 is shown as viewed from the inner-surface side of the substrate 12. As shown in FIG. 4, the internal contact 36 is attached to the inner surface 16 of the substrate 12 by bond 42, which is shown in dashed lines to indicate that the bond is not visible in this view of assembly 10. Also shown in FIG. 4 is external contact 32 hermetically sealed to the outer surface of substrate 12 by bond 40.

In one or more embodiments, the internal contact 36 can be smaller than the external contact 32 in a dimension in the plane parallel to the inner surface 16. In one or more embodiments, the internal contact 36 can be the same dimension or dimensions as external contact 32. In one or more embodiments, the internal contact 36 can be larger than the external contact 32 in a dimension in the plane parallel to the inner surface 16. Further, the internal contact 36 can take the same shape or combination of shapes as the external contact 32. In one or more embodiments, the internal contact 36 can take a shape that is different from the shape of the external contact 32.

In one or more embodiments, the external contact 32 can be larger than the internal contact 36 such that the internal contact 36 can first be attached to the inner surface 16 of substrate 12, e.g., by directing light through the substrate from the external surface 14 to an interface of the internal contact 36 and the inner surface 16 of the substrate to form bond 42. The external contact 32 is connected to the outer surface 14 of the substrate 12 by directing light through the internal surface 16 to an interface of the external contact 32 and the outer surface 14 to form bond 40 without the internal contact 36 being between the light and the region where the bond 42 is formed. In one or more embodiments, the external contact 32 and the internal contact 36 can be relatively the same size. In such embodiments, the external contact 32 and/or the internal contact 36 can be attached to the substrate 12 in any suitable order. For example, the external contract 32 can be attached to the outer surface 14 of the substrate 12 using light to form bond 40. The internal contact 36 can then be attached to the inner surface 16 of the substrate 12 by directing light at an angle into the substrate from the external surface 14 such that the external contact 32 does not block the light as it forms bond 42 to attach the internal contact 36 to the internal surface 16 of the substrate 12. In accordance with some embodiments, one or both of the external contact 32 and the internal contact 36 is/are bonded to the outer surface 14 and the inner surface 16, respectively, to form a hermetic seal. In other embodiments, only one of the bonds 40, 42 is formed as a hermetic seal.

As with bond 40, bond 42 can, in one or more embodiments, take any suitable shape or combination of shapes and have any suitable dimensions, e.g., the shapes and dimensions described for bond 40. For example, as illustrated in FIG. 4, bond 42 can include a bond line 43. In one or more embodiments, bond 42 can include any suitable size and shaped region or regions that surround the via 20. Further, as is also the case with bond 40, bond 42 can include an interfacial layer between the inner surface 16 of the substrate 12 and the internal contact 36. This interfacial layer can have any suitable thickness, e.g., the same thicknesses as those described for bond 40. In one or more embodiments, the bond 42 can be a laser bond.

As illustrated in FIG. 1B, the weld ring 60 can optionally provide electrical coupling to the substrate 12. For example, weld ring 60 can be electrically connected to a ground terminal 37 that is, for example, on an enclosure or housing of an implantable medical device that includes the assembly 10. In implementations where the weld ring 60 material is not conductive, weld ring 60 can include one or more vias 62 for electrical coupling to the ground terminal 37. In an alternative embodiment, the weld ring 60 can be formed from a conductive material thereby obviating the need for the vias 62. In the example embodiment of FIG. 1B, vias 20 can be utilized to electrically couple a contact on the inner surface 16, such as internal contact 36, to the weld ring 60.

As mentioned herein, any suitable conductors or contacts can be formed on one or both of the inner surface 16 and the outer surface 14 of the substrate 12. For example, as shown in FIGS. 1A-1B, one or more conductors 50 can be formed on the outer surface 14 of the substrate 12. Further, one or more conductors 52 can be disposed on the inner surface 16. Any suitable number of conductors can be formed on one or both of the outer surface 14 and the inner surface 16. Any suitable technique or combination of techniques can be utilized to form conductors 50, 52, e.g., chemical vapor deposition, plasma vapor deposition, physical vapor deposition, plating, etc., followed by photolithography, chemical etching, etc. In other example embodiments, a conductive material layer can be formed on one or both of the outer surface 14 and inner surface 16, and the conductive material layer can be patterned to form conductors 50, 52. Further, the conductors 50, 52 can include any suitable conductive material or combination of conductive materials. In one or more embodiments, the conductor 50 can electrically couple two or more external contacts 32 together, and conductor 52 can electrically couple two or more internal contacts 36 together. In one or more embodiments, any of conductors 50, 52 can be coupled to one or more suitable electronic device(s). In one or more embodiments, one or both of conductors 50, 52 can be formed to provide an antenna for communication with one or more electronic devices electrically coupled to the feedthrough assembly 10. Further, in one more embodiments, one or both of conductors 50, 52 can form an inductive coil that can be utilized to provide inductive coupling to an external inductive power supply. For example, if the feedthrough assembly 10 is included in an implantable medical device, then conductor 50 can be used to form an inductive coil that can receive inductive energy from an external inductive power supply to provide power to the implantable medical device. Alternatively, the inductive coil can be formed by patterning the external contacts 32.

Figure 15:
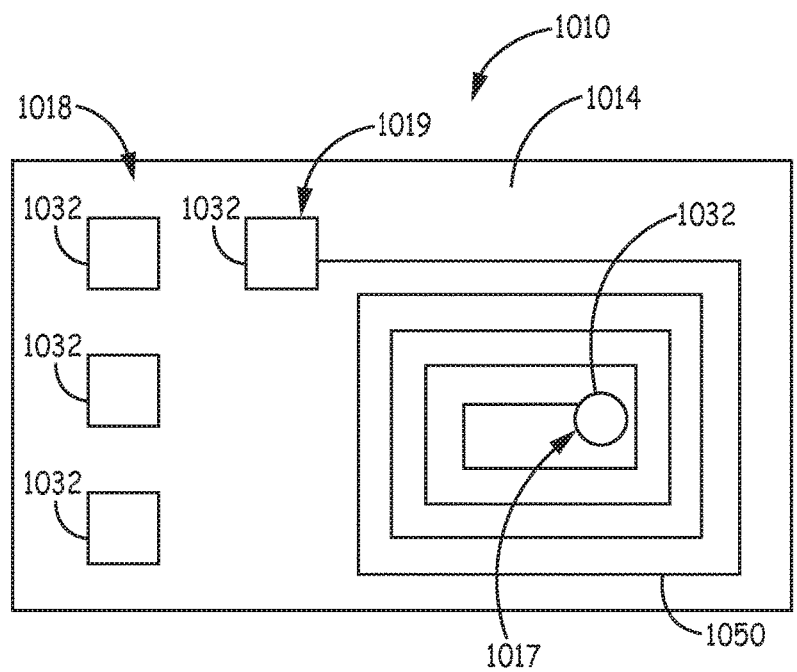
FIG. 15 is a schematic plan view of another embodiment of a feedthrough assembly.

For example, FIG. 15 is a schematic plan view of another embodiment of a feedthrough assembly 1010. All of the design considerations and possibilities regarding the feedthrough assembly 10 of FIGS. 1A-4 apply equally to the feedthrough assembly 1010 of FIG. 15. Assembly 1010 includes feedthroughs 1018. Each feedthrough 1018 includes an external contact 1032 that can be electrically coupled to an internal contact, conductor, or device. The assembly 1010 also includes a conductor 1050 that is electrically coupled to external contact 1032 of feedthrough 1019 and external contact 1032 of feedthrough 1017. In one or more embodiments, the conductor 1050 is adapted to form an antenna that can provide wireless communication to one or more electronic devices disposed within a package that is attached to the feedthrough assembly 1010, e.g., electronic device 6 of package 2 of FIGS. 1A AND 1B. In one or more embodiments, the conductor 1050 can be adapted to form an inductive coil that can be inductively coupled with a power source to provide power to one or more devices electrically coupled to feedthroughs 1017 and 1019.

The conductors 50, 52 of FIGS. 1A-4 can take any suitable shape or combination of shapes and have any suitable dimensions. Further, one or more conductors 50, 52 can electrically couple the assembly 10 to ground, e.g., through coupling ground terminal 37 to an enclosure or housing of an implantable medical device that includes the assembly 10.

Each of the conductors 50, 52 can be formed in separate steps. In one or more embodiments, conductors on either or both of the outer surface 14 and inner surface 16 can be formed simultaneously with the conductive material 22 disposed in the via and/or the external or internal contacts 32, 36.

In one or more embodiments, one or more conductors 50, 52 can be disposed such that the conductors are electrically coupled to a contact and the conductive material 22 disposed in the via 20. In such embodiments, the bond 40 and/or the bond 42 would be formed between the contact, the conductor, and the substrate 12 such that electrical coupling between the contact, the conductor, and the conductive material is maintained.

The electronic device 6 can be electrically coupled to one or more internal contacts 36 of the assembly using any suitable technique or combination of techniques. For example, in one or more embodiments, solder bumps and/or contact pads of the electronic device 6 can be directly attached to one or more internal contacts 36 using any suitable technique or combination of techniques, e.g., soldering, welding, laser bonding, etc. In one or more embodiments, one or more conductors (not shown) can be electrically coupled to one or more internal contacts 36 and one or more solder bumps and/or contact pads of the electronic device 6 using any suitable technique or combination of techniques, e.g., soldering, welding, laser bonding, etc.

The package 2 of FIGS. 1A AND 1B can be electrically coupled to any suitable device or devices that are external to the package. For example, in one or more embodiments, the package 2 can be electrically coupled to a lead of an implantable medical device. In one or more embodiments, the package 2 can be electrically coupled to a power source or sources. Further, in one or more embodiments, the package 2 can be electrically coupled to one or more therapeutic electrodes that can be utilized for delivering and/or receiving one or more electric signals to a patient, either while the package is outside or inside the patient. Any suitable technique or combination of techniques can be utilized to electrically couple the package 2 to one or more devices, e.g., welding, soldering, mechanically fastening, adhering with a conductive adhesive, magnetic coupling, etc.

The package 2 can be coupled to one or more external devices using any other type of coupling. For example, the package 2 can be wirelessly coupled to a device through one or more antenna(s) disposed either on an outer surface of the package (e.g., antenna 1050 of feedthrough assembly 1010 of FIG. 15) or within the package. Further, in one or more embodiments, the package 2 can be inductively coupled to one or more external devices through one or more inductive coils disposed either on a surface of the package or within the package.

Figure 5:
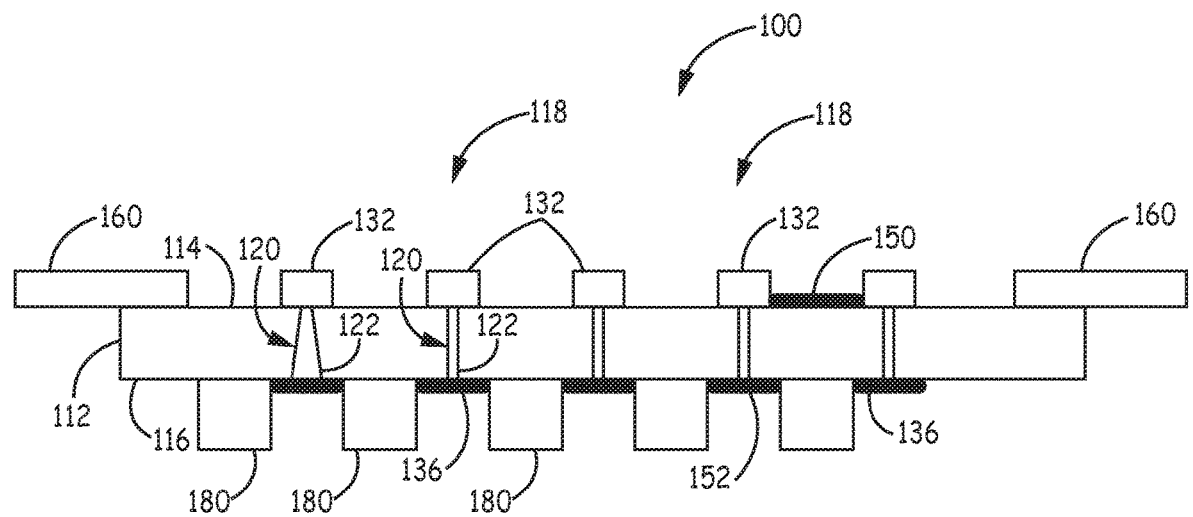
FIG. 5 is a schematic cross-section view of another embodiment of a feedthrough assembly.

The feedthrough assemblies described herein can include any suitable additional elements or devices. For example, FIG. 5 is a schematic cross-section view of another embodiment of a feedthrough assembly 100. All of design considerations and possibilities regarding the assembly 10 of FIGS. 1A-4 apply equally to the assembly 100 of FIG. 5. The assembly 100 includes a substrate 112 having an outer surface 114 and an inner surface 116, and one or more feedthroughs 118. The feedthrough 118 can include a via 120 from the outer surface 114 to the inner surface 116. Conductive material 122 can be disposed in one or more of the vias 120. The feedthrough 118 can also include an external contact 132 disposed over the via 120 on the outer surface 114 of the substrate 112, where the external contact is electrically coupled to the conductive material 122 disposed in the via 120. In one or more embodiments, the external contact 132 can be hermetically sealed to the external surface 114 of the substrate 112 by a bond that surrounds the via 120 (e.g., bond 40 of FIG. 4). Further, in one or more embodiments, the feedthrough 118 can include an internal contact 136 disposed over the via 120 on the inner surface 116, where the internal contact is electrically coupled to the conductive material 122 disposed in the via 120. The internal contact 136 can be formed by any suitable technique such as sputtering, plating, evaporating, etc.

One difference between assembly 100 and assembly 10 is that assembly 100 includes one or more electronic devices 180 disposed on the inner surface 116 of the substrate 112. Any suitable electronic device can be disposed on, or connected to, the inner surface 116, e.g., capacitors, transistors, integrated circuits, including controllers and multiplexers, etc. Further, any suitable number of electronic devices 180 can be disposed on the inner surface 116. Any suitable technique or combination of techniques can be utilized to dispose the electronic device 180 on the inner surface 116. In one or more embodiments, the electronic device 180 can be formed on the inner surface 116 of the substrate 112. In one or more embodiments, the device 180 can be formed separately and then attached to the inner surface 116. Any suitable technique or combination of techniques can be utilized to attach the electronic device 180 to the substrate 112, e.g., a bond (e.g., bond 40 of FIG. 4) can be formed between the electronic device and the inner surface 116 of the substrate.

The electronic device 180 can be electrically coupled to one or more additional electronic devices disposed on the inner surface 116. In one or more embodiments, the electronic device 180 can be electrically coupled to the conductive material 122 disposed in one or more vias. Any suitable technique or combination of techniques can be utilized to electrically couple the electronic device 180 to the conductive material 122, e.g., one or more conductors 152 can be disposed on the inner surface 116, or the electronic device 180 can be attached to the internal contact 136. Further, in one or more embodiments, the electronic device 180 can be electrically coupled to other electronic circuitry or devices disposed adjacent the substrate 112. In one or more embodiments, the feedthrough 118 can provide a conductive pathway from the outer surface 114 to the electronic device 180.

Figure 6:
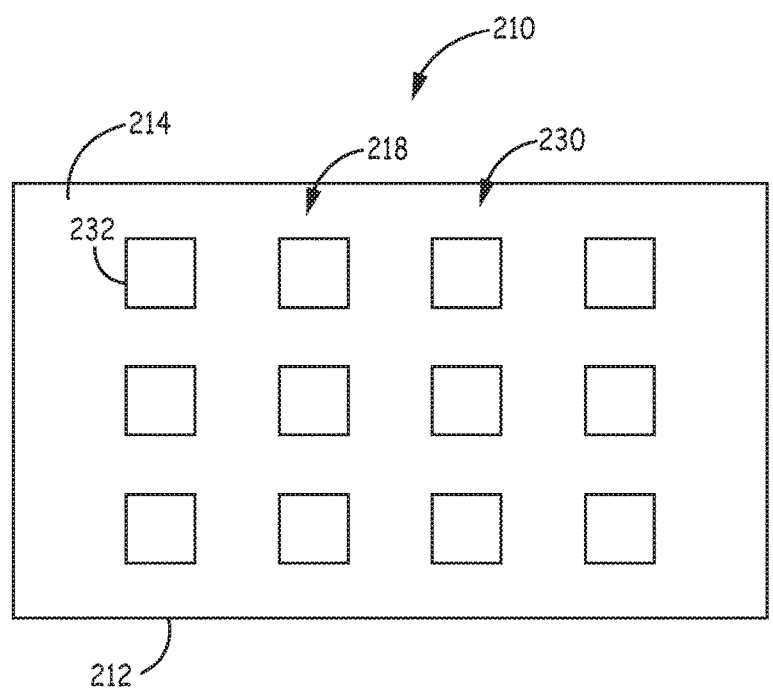
FIG. 6 is a schematic plan view of another embodiment of a feedthrough assembly.

As mentioned herein, the various embodiments of feedthrough assemblies described herein can include any suitable number of feedthroughs. The feedthroughs can be disposed in any suitable arrangement. In one or more embodiments, the feedthroughs can be disposed in a random configuration. In one or more embodiments, the feedthroughs can be disposed in an array. For example, FIG. 6 is a schematic plan view of one embodiment of a feedthrough assembly 210. All of the design considerations and possibilities regarding the feedthrough assembly 10 of FIGS. 1A-4 apply equally to the feedthrough assembly 210 of FIG. 6. The feedthrough assembly 210 includes feedthroughs 218 formed through substrate 212. The feedthroughs 218 are disposed in an array 230. The array 230 can include any suitable number of feedthroughs 218. And the feedthrough array 230 can include any suitable arrangement of feedthroughs 232.

The various embodiments of feedthrough assemblies (e.g., feedthrough assembly 10 of FIGS. 1A-4) described herein can be formed using any suitable technique or combination of techniques. In general, the feedthrough assemblies described herein can be formed as single assemblies. In one or more embodiments, two or more feedthrough assemblies can be formed on a substrate and then singulated using any suitable technique or combination of techniques.

Figure 7A:
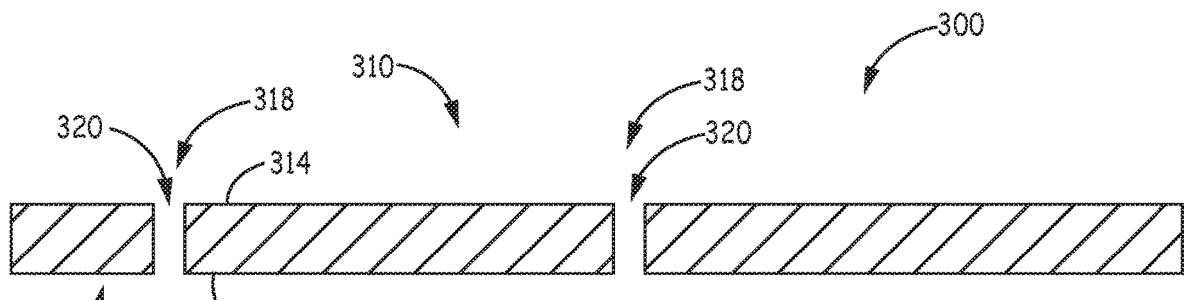
FIG. 7A is a schematic cross-section view of an embodiment of a method of forming a feedthrough assembly.

FIGS. 7A-E are schematic views of one embodiment of a method 300 of forming a feedthrough assembly 310. All of the design considerations and possibilities regarding the feedthrough assembly 10 of FIGS. 1A-4 apply equally to feedthrough assembly 310 of FIGS. 7A-E. In FIG. 7A, a substrate 312 is provided. An exterior surface 314 and an interior surface 316 of the substrate 312 can be prepared by polishing to remove surface deformities such as burrs, gouges, ridges, or other irregularities. Different techniques may be used to polish outer surface 314 and inner surface 316. For example, surfaces 314, 316 can be mechanically polished, chemically polished, or treated by chemical-mechanical polishing (CMP) techniques. Surfaces 314, 316 can be polished until the surfaces exhibit comparatively low surface roughness values that enhance direct bond formation. Although surfaces 314, 316 may be polished to remove irregularities, the bonding process according to the present disclosure may not require the surfaces to be as smooth as surfaces used during typical wafer bonding techniques. Surfaces 314, 316 may be cleaned to remove particles and contaminates. Cleaning surfaces 314, 316 can include ultrasonic and/or megasonic cleaning.

One or more feedthroughs 318 can be formed through the substrate 312. The feedthrough 318 can be formed by forming a via 320 through the substrate 312. Although feedthrough assembly 310 includes two feedthroughs 318, any suitable number of feedthroughs may be formed, e.g., 1, 2, 3, 4, 5, or more feedthroughs. Further, any suitable technique or combination of techniques can be utilized to form via 320, e.g., drilling, etching, laser drilling, etc.

Figure 7B:
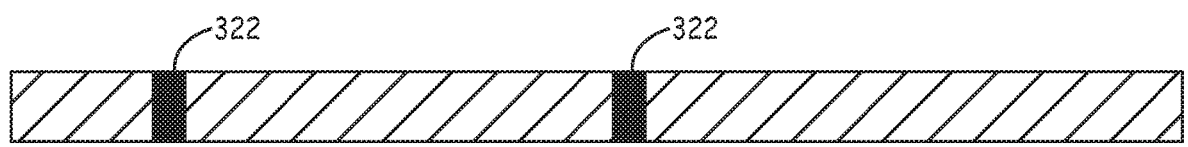
FIG. 7B is a schematic cross-section view of an embodiment of a method of forming a feedthrough assembly.

Conductive material 322 can be formed in the via 320 as shown in FIG. 7B. Any suitable technique or combination of techniques can be utilized to form or dispose the conductive material 322 in the via 320, e.g., plasma vapor deposition, chemical vapor deposition, physical vapor deposition (e.g., sputtering), plating, conductive composite pastes, etc. Further, the conductive material 322 may substantially fill the via 320. In one or more embodiments, conductive material can be formed on one or more sidewalls of the via to form or dispose one or more conductors within the via.

In one or more embodiments, one or both of the outer surface 314 and the inner surface 316 can be polished to remove any excess conductive material 322. Any suitable technique or combination techniques can be utilized to polish one or both surfaces 314, 316.

Figure 7C:
FIG. 7C is a schematic cross-section view of an embodiment of a method of forming a feedthrough assembly.

One or more conductors 350 can optionally be formed on at least one of the outer surface 314 and the inner surface 316. As illustrated in FIG. 7C, conductors 350 are formed on the outer surface 314 of the substrate 312. Any suitable technique or combination of techniques can be utilized to form conductors 350. For example, in one or more embodiments, conductors 350 are formed by depositing a conductive material layer on the outer surface 314 and the conductive material 322. The conductive material layer can be formed, e.g., using plasma vapor deposition, chemical vapor deposition, physical vapor deposition, etc. One or more portions of the conductive material layer can then be removed to form the conductors 350 using any suitable technique or combination of techniques, e.g., photolithography, etc. In one or more embodiments, the conductors 350 are patterned such that the conductors remain electrically coupled to conductive material 322 of via 320. Any suitable number of conductors 350 can be formed on the outer surface 314 and/or the inner surface 316 of substrate 312.

In one or more embodiments, the conductors 350 are electrically coupled to the conductive material 322 in the vias 320. In such embodiments, the conductors 350 can be electrically coupled using any suitable technique, e.g., the electrical conductors are in physical contact with the conductive material. In one or more embodiments, the conductors 350 and the conductive material 322 can include the same material or combination materials. Further, in one or more embodiments, the conductors 350 and the conductive material 322 can be formed or disposed simultaneously or sequentially.

Figure 7D:
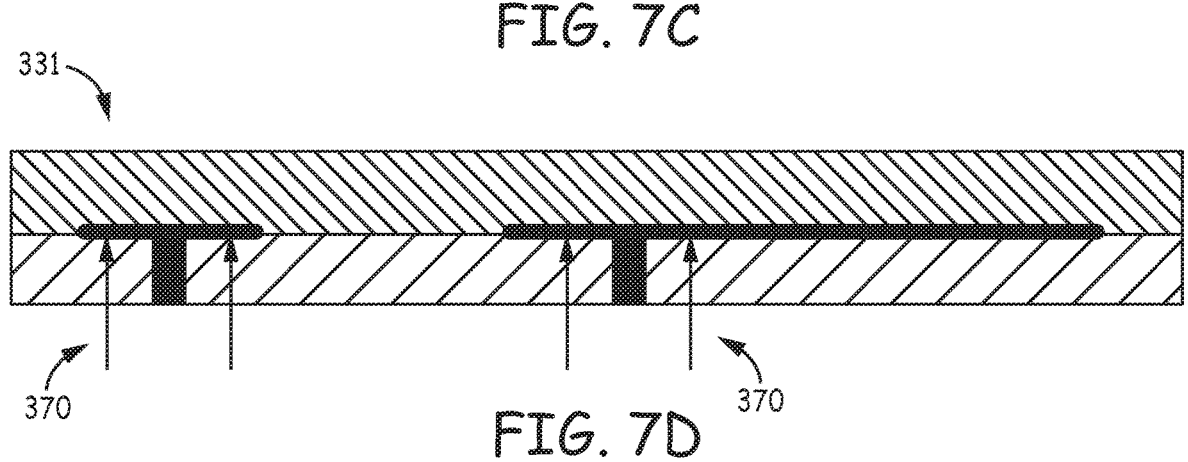
FIG. 7D is a schematic cross-section view of an embodiment of a method of forming a feedthrough assembly.

One or more contacts can be formed on one or both of the outer surface 314 and the inner surface 316 of substrate 312 using any suitable technique or combination of techniques. For example, as illustrated in FIG. 7D, a conductive material layer 331 can be disposed on and/or coupled to the outer surface 314 over the conductors 350 (if present) and the vias 320. In an embodiment, the conductive material layer 331 can comprise a conductive sheet or foil. The conductive material layer 331 can be attached to the outer surface 314 of the substrate 312 using any suitable technique or combination of techniques, e.g., forming a bond that hermetically seals the conductive layer to the outer surface. Although not shown, a second conductive material layer can also be formed on the inner surface 316 and over the vias 320. In such embodiments, the conductive material layers can be formed simultaneously on both surfaces of substrate 312 or sequentially. The conductive material layer 331 can be attached to the outer surface 314 as illustrated in FIG. 7D.

Any suitable technique or combination of techniques can be utilized to attach the conductive layer 331 to the outer surface 314, e.g., the techniques described in U.S. Patent Application No. 62/096,706 (Medtronic Reference No. C00008775.USP1), entitled KINETICALLY LIMITED NANO-SCALE DIFFUSION BOND STRUCTURES AND METHODS. For example, electromagnetic radiation 370 can be directed through substrate 312 from the inner surface 316 to an interface between the conductive layer 331, the conductors 350 (if present), and a surface of the substrate 312. The electromagnetic radiation 370 can form a bond (e.g., bond 40 of FIGS. 2 and 4) that hermetically seals the conductive layer 331 to the substrate 312 in any suitable pattern or shape. The bond can be a laser bond. In one or more embodiments, a bond surrounds the via 320.

Figure 7E:
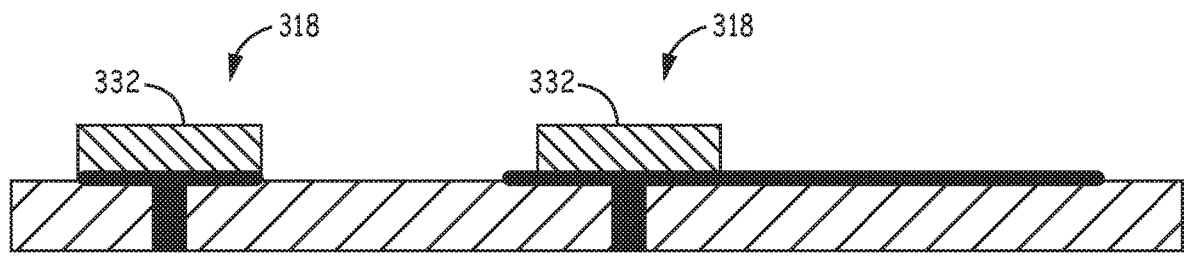
FIG. 7E is a schematic cross-section view of an embodiment of a method of forming a feedthrough assembly.

As illustrated in FIG. 7E, one or more portions of the conductive material layer 331 can be removed to form an external contact 332 on the outer surface 314 of the substrate 312. Any suitable technique or combination of techniques can be utilized to form the external contacts 332, e.g., photolithography, etching, laser ablation, etc. In one or more embodiments, a mask or masks can be formed on the outer surface 314 of the substrate 312, and the conductive material layer 331 can be formed over the mask. Portions of the conductive material layer 331 that are formed on the mask itself can be removed using any suitable technique or combination of techniques, including photolithography, etching, laser ablation etc., to form external contacts 332. In addition, one or more portions of the conductive material layer 331 can also be removed or patterned to create other electrical components, such as an antenna.

The bond formed between the external contact 332 and the outer surface 314 remains intact such that it hermetically seals the contact to the outer surface 314. In other words, portions of the conductive layer 331 that are hermetically sealed to the outer surface 314 are not removed when the external electrodes 332 are patterned. Similar techniques can be utilized to form internal contacts on the inner surface 316 of the substrate 312. The external contact 332 is electrically coupled to both the conductors 350 (if present) and the conductive material 322 formed in the via 320. One or more feedthroughs 318 are thus formed through the substrate 312 to provide conductive pathways between the outer surface 314 and the inner surface 316.

Figure 8A:
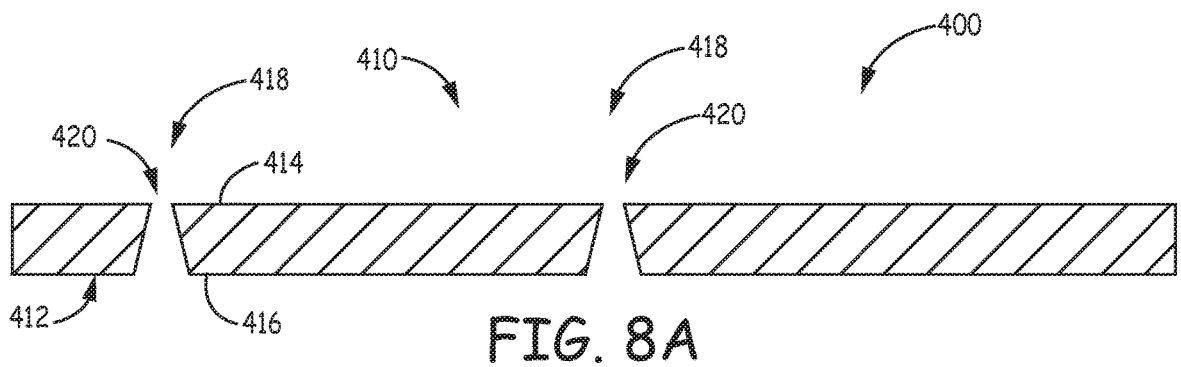
FIG. 8A is a schematic cross-section view of another embodiment of a method of forming a feedthrough assembly.
Figure 8B:
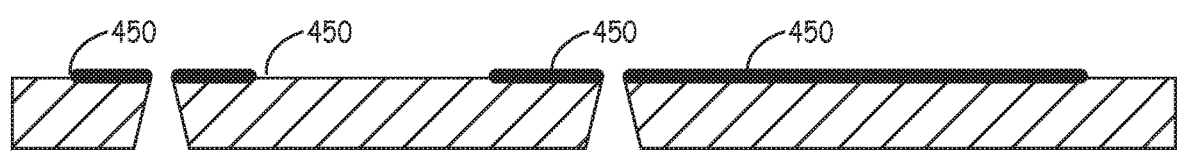
FIG. 8B is a schematic cross-section view of another embodiment of a method of forming a feedthrough assembly.

FIGS. 8A-E are schematic cross-section views of another method 400 of forming a feedthrough assembly 410. All of the design considerations and possibilities regarding the feedthrough assembly 10 of FIGS. 1A-4 and feedthrough assembly 310 of FIGS. 7A-E apply equally to the feedthrough assembly 410 of FIGS. 8A-E. One or more feedthroughs 418 can be formed through a substrate 412. A via 420 can be formed through the substrate 412 between an outer surface 414 and an inner surface 416 of the substrate as shown in FIG. 8A. Any suitable technique or combination of techniques can be utilized to form via 420. One or more conductors 450 can be formed on at least one of the outer surface 414 and the inner surface 416 using any suitable technique or combination of techniques as shown in FIG. 8B. For example, in one or more embodiments, a conductive material layer can be formed on one or both of the outer surface 414 and inner surface 416, and the conductive material layer can be patterned to form conductors 450. The conductors 450 can include any suitable conductors, e.g., conductors 50 of assembly 10. The conductors 450 can be formed such that they are electrically coupled to the via 420.

Figure 8C:
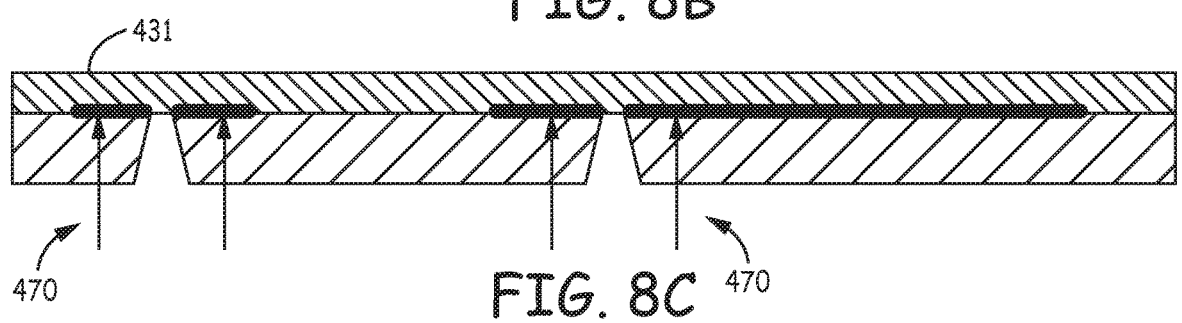
FIG. 8C is a schematic cross-section view of another embodiment of a method of forming a feedthrough assembly.

As shown in FIG. 8C, a conductive material layer 431 can be formed on the outer surface 414 of the substrate 412. In one or more embodiments, the conductive material layer 431 can also be formed over one or more of the conductors 450 and one or more of the vias 420. Further, in one or more embodiments, a conductive material layer can also be formed on the inner surface 416 of the substrate 412.

The conductive material layer 431 can be attached to the outer surface 414 of the substrate 412 using any suitable technique or combination of techniques. As illustrated in FIG. 8C, the conductive material layer 431 is attached to the outer surface 440 by directing electromagnetic radiation 470 through the inner surface 416 of the substrate 412 and directing the light at an interface of the conductive material layer 631 and the outer surface 414. In one or more embodiments, the light 470 can be directed and/or focused on the conductors 450 that are disposed between the conductive layer 431 and the outer surface 414. The light 470 can form a bond between the conductive layer 431 and the outer surface 414 (e.g., bond 40 of FIGS. 2 and 4). In one or more embodiments, the conductors 450 can also be attached to one or both of the conductive of layer 431 and the outer surface 414 along the bond. Bonding the conductors 450 along or within the bond can further enhance electrical coupling between the conductive layer and the conductors. Further, in one or more embodiments, the bond can hermetically seal the conductive layer 431 to the outer surface 414 of the substrate 412.

Figure 8D:
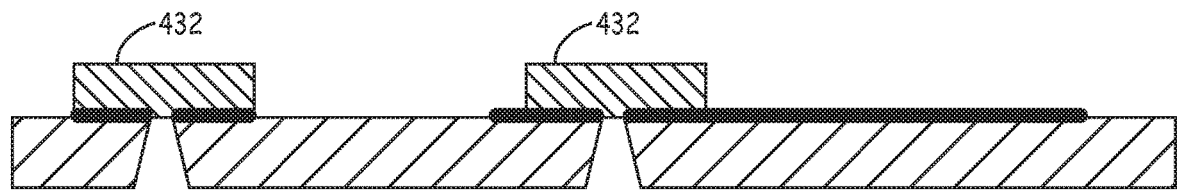
FIG. 8D is a schematic cross-section view of another embodiment of a method of forming a feedthrough assembly.

A portion or portions of the conductive material layer 431 can be removed to form one or more external contact 432 on the outer surface 414 of the substrate 412 as shown in FIG. 8D. These portions of the conductive material layer 431 can be removed using any suitable technique or combination of techniques. Any suitable technique or combination of techniques can be utilized to form the external contacts 432 including, for example, photolithography, etching, laser ablation, etc. In some embodiments, a mask or masks can be formed on the outer surface 414 of the substrate 412, and the conductive material layer 431 can be formed over the mask. Portions of the conductive material layer 431 that are formed on the mask itself can be removed using any suitable technique or combination of techniques to form external contacts 432. In one or more embodiments, the bond formed between the conductive material layer 431 and the substrate 412 when the conductive material layer was attached to the substrate remains between the external contact 432 and the outer surface 414 of the substrate such that the external contact is hermetically sealed to the outer surface of the substrate.

Figure 8E:
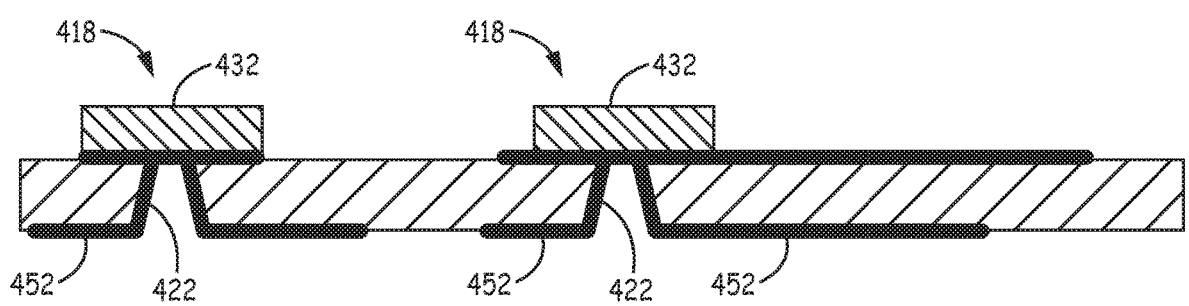
FIG. 8E is a schematic cross-section view of another embodiment of a method of forming a feedthrough assembly.

Conductive material 422 can be formed in via 420 as shown in FIG. 8E using any suitable technique or combination of techniques. In one or more embodiments, the conductive material 422 fills substantially all of the via 420 to provide a conductive pathway from the external contact 432 and the conductors 450 on the outer surface 414 of the substrate 412 to one or more conductors or contacts on the inner surface 416 or one or more electronic devices disposed on the inner-surface side of the substrate. In one or more embodiments, conductive material 422 can form one or more conductors within the via to provide this conductive pathway. For example, the conductive material 422 can be disposed on one or more sidewalls of the via 420 to provide a conductive pathway. Because the external contact 432 is hermetically sealed to the outer surface 414 of the substrate 412, the via 420 does not need to be substantially filled with conductive material to hermetically seal the feedthrough 418. Discrete conductors, therefore, can be formed in the via 420.

The conductive material 422 is electrically coupled to the external contact 432. In one or more embodiments, the conductive material 422 can also be electrically coupled to the conductors 450. Further, in one or more embodiments, the conductive material 422 can also be formed on the inner surface 416 of the substrate to provide one or more conductors 452. In one or more embodiments, a separate conductive material can be formed on the inner surface 416 to provide one or more conductors on the inner surface. The conductive material 422 can be disposed in the via 420 and form conductors 452 either simultaneously or sequentially.

Figure 9A:
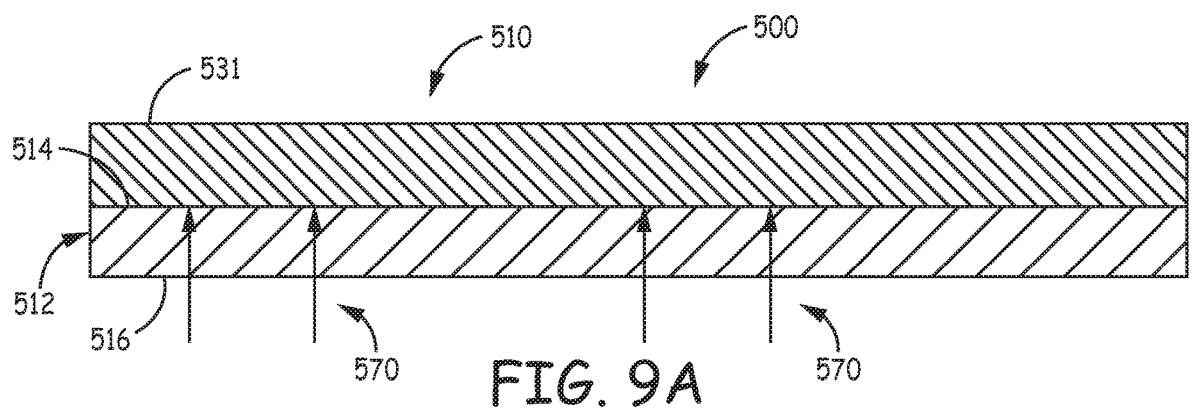
FIG. 9A is a schematic cross-section view of another embodiment of a method of forming a feedthrough assembly.

FIGS. 9A-E are schematic cross-section views of another embodiment of a method 500 for forming a feedthrough assembly 510. All of the design considerations and possibilities regarding the feedthrough assembly 10 of FIGS. 1A-4, feedthrough assembly 310 of FIGS. 7A-E, and feedthrough assembly 410 of FIGS. 8A-E apply equally to the feedthrough assembly 510 of FIGS. 9A-E. In method 500, a conductive material layer 531 can comprise a conductive sheet or foil as described in conjunction with FIGS. 7A-E. The conductive material layer 531 can be attached to the outer surface 514 of the substrate 512 using any suitable technique or combination of techniques, e.g., forming a bond that hermetically seals the conductive layer to the outer surface. For example, as illustrated in FIG. 9A, electromagnetic radiation 570 is directed through inner surface 516 of the substrate 512 and directed at an interface of the conductive material layer 531 and the outer surface 514 to form one or more bonds between the conductive material layer 531 and the outer surface.

Figure 9B:
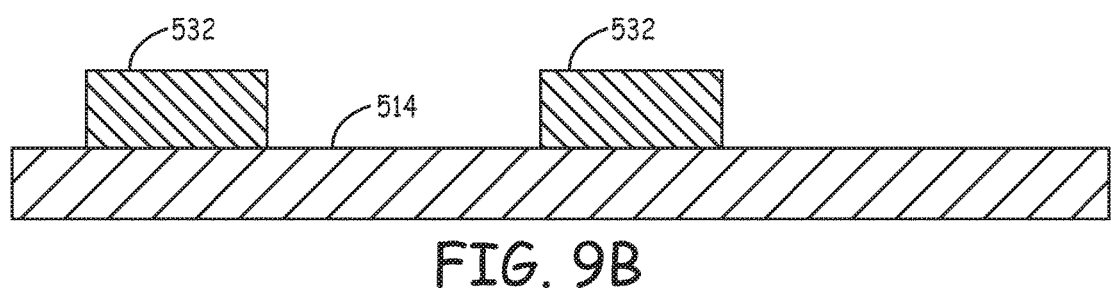
FIG. 9B is a schematic cross-section view of another embodiment of a method of forming a feedthrough assembly.

One or more portions of the conductive material layer 531 can be removed to form one or more external contacts 532 on the outer surface 514 of the substrate 512 as shown in FIG. 9B. Any suitable technique or combination of techniques can be utilized to form the external contacts 532 including, for example, photolithography, etching, laser ablation, etc. In some embodiments, a mask or masks can be formed on the outer surface 514 of the substrate, and the conductive material layer 531 can be formed over the mask. Portions of the conductive material layer 531 that are formed on the mask itself can be removed using any suitable technique or combination of techniques to form external contacts 532. In one or more embodiments, the bond formed when the conductive material layer 531 was attached to the substrate 512 remains between the external contact 532 and the outer surface 514 of the substrate 512 such that the contact is hermetically sealed to the outer surface. Any suitable technique or combination of techniques can be utilized to form external contacts 532.

Figure 9C:
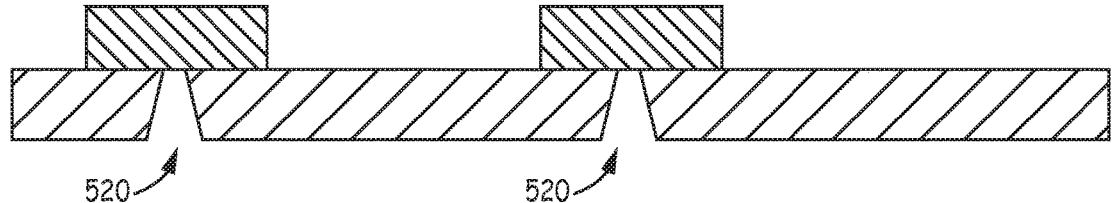
FIG. 9C is a schematic cross-section view of another embodiment of a method of forming a feedthrough assembly.

As shown in FIG. 9C, one or more vias 520 can be formed through the substrate 512. The via 520 can be formed such that it is within a closed shape or region defined by the bond such that the bond surrounds the via. Because the via 520 is within the shapes or regions formed by the bonds, the via 520 can be protected from the external environment. In one or more embodiments, an etch stop layer can be formed between the conductive material layer 531 and the outer surface 514 of the substrate 512 to prevent the formation of the via 520 from removing portions of the external contact 532.

Figure 9D:
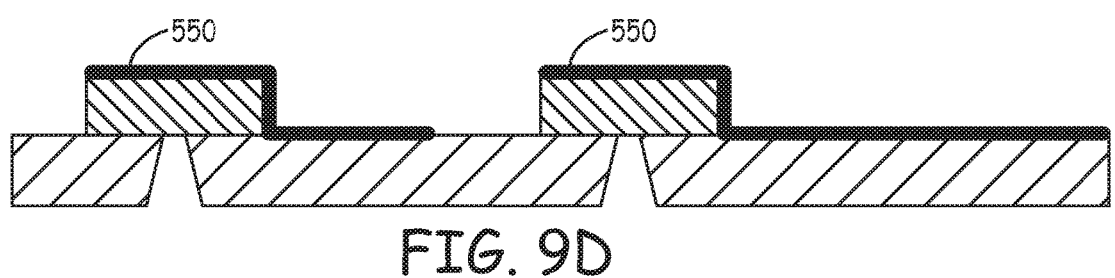
FIG. 9D is a schematic cross-section view of another embodiment of a method of forming a feedthrough assembly.

One or more conductors 550 can optionally be formed on the external contact 532 and/or on the outer surface 514 of the substrate 512 as shown in FIG. 9D. In one or more embodiments, one or more conductors 550 can be electrically coupled to the external contact 532. Any suitable technique or combination of techniques can be utilized to form conductors 550. In one or more embodiments, the conductors 550 can be provided by forming a conductive material layer over the external contact 532 and the outer surface 514. This conductive material layer can then be patterned to form conductor 550 in any desirable configuration.

Figure 9E:
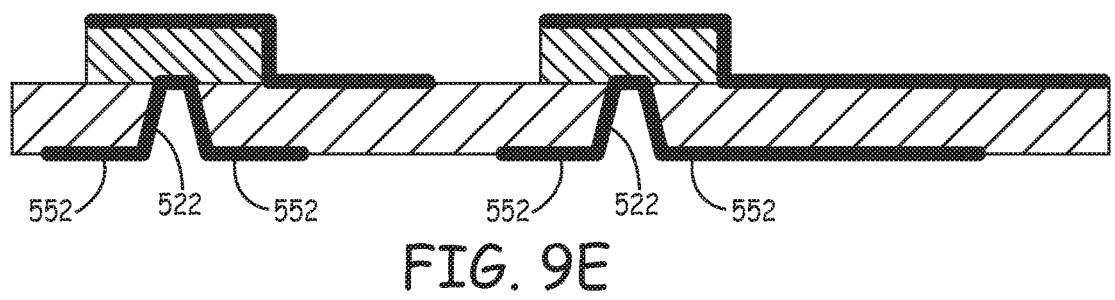
FIG. 9E is a schematic cross-section view of another embodiment of a method of forming a feedthrough assembly.

As shown in FIG. 9E, conductive material 522 can be disposed in the via 520 to provide a conductive pathway from the external contact 532 to conductors, contacts, electronic devices, etc. disposed on the inner-surface side of the substrate 512. Any suitable technique or combination of techniques can be utilized to form the conductive material 522 in the via 520. As mentioned herein, the via 520 can be substantially filled with the conductive material 522. In one or more embodiments, the conductive material 522 can be disposed on a portion or portions of one or more sidewalls of the vias as shown in FIG. 9E. Further, one or more conductors 552 can optionally be formed on the inner surface 516 of the substrate 512 either simultaneously with forming conductive material in the vias or sequentially. In one or more embodiments, the same material utilized for the conductive material 522 can also be utilized to form conductors 552. Conductors 552 can be formed using any suitable technique or combination of techniques. The optional conductors 550 can be provided to, for example, electrically couple an electronic device or contact disposed on the outer surface 514 to the conductors 552, or a contact or electronic device on the inner surface 516.

The various embodiments of hermetically-sealed packages and feedthrough assemblies described herein can be utilized with any device or system that requires hermetically sealed conductive pathways. For example, one or more embodiments of feedthrough assemblies described herein can be utilized with an implantable medical device or system. Nearly any implantable medical device or system employing leads may be used in conjunction with the various embodiments of packages and feedthrough assemblies described herein. Representative examples of such implantable medical devices include hearing implants, e.g., cochlear implants; sensing or monitoring devices; signal generators such as cardiac pacemakers or defibrillators, neurostimulators (such as spinal cord stimulators, brain or deep brain stimulators, peripheral nerve stimulators, vagal nerve stimulators, occipital nerve stimulators, subcutaneous stimulators, etc.), gastric stimulators; or the like.

Figure 10:
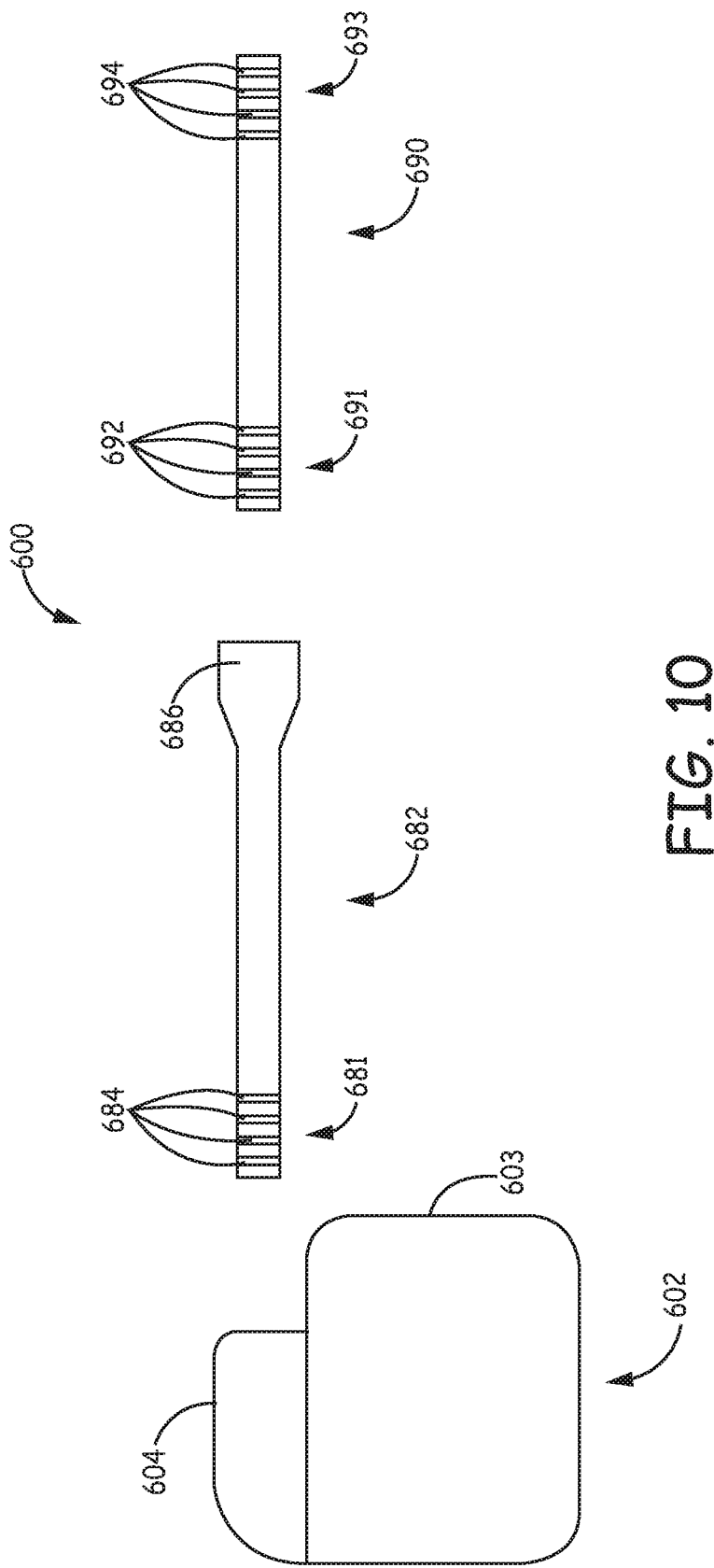
FIG. 10 is a schematic side view of one embodiment of an implantable medical device system.

For example, FIG. 10 is a schematic side view of one embodiment of an implantable medical device system 600. The system 600 includes an implantable medical device (IMD) 602, a lead 690, and a lead extension 682. In one or more embodiments, the system 600 can also include a feedthrough assembly (e.g., feedthrough assembly 10 of FIGS. 1A-4).

The IMD 602 includes a connector header 604 adapted to receive a proximal portion 681 of the lead extension 682. The proximal portion 681 of lead extension 682 includes one or more electrical contacts 684 that are electrically coupled to internal contacts (not shown) at distal connector 686 of the lead extension. The connector header 604 of the IMD 602 includes internal contacts (not shown) and is adapted to receive the proximal portion 681 of the lead extension 682 such that the internal contacts of the connector header may be electrically coupled to the contacts 684 of the lead extension when the lead extension is inserted into the header.

The system 600 depicted in FIG. 10 further includes lead 690. The depicted lead 690 has a proximal portion 691 that includes contacts 692 and a distal portion 693 that includes electrodes 694. Each of the electrodes 694 can be electrically coupled to a discrete contact 692. The distal connector 686 of the lead extension 682 is adapted to receive the proximal portion 691 of the lead 690 such that the contacts 692 of the lead may be electrically coupled to the internal contacts of the connector of the extension. Accordingly, a signal generated by the IMD 602 can be transmitted to a tissue of a patient by an electrode 694 of lead 690 when the lead is connected to the extension 682 and the extension is connected to the IMD. Alternatively or in addition, a signal received by electrode 694 of lead 690 from a patient may be transmitted to a contact of the IMD 602 when the lead is connected to the extension 682 and the extension is connected to the IMD.

It will be understood that lead 690 can be coupled to IMD 602 without use of an extension 682. Any number of leads 690 or extensions 682 can be coupled to device 602. While lead 690 is depicted as having four electrodes 694, it will be understood that the lead can include any number of electrodes, e.g. 1, 2, 3, 4, 5, 6, 7, 8, 16, 32, or 64 electrodes. Corresponding changes in the number of contacts 692 in lead 690, contacts 684 and internal contacts in connector 686 of lead extension, or internal contacts in header 604 of device 602 may be required or desired.

As used hereinafter, "lead" will refer to both "leads" and "lead extensions" unless the content and context clearly dictates otherwise.

Figure 11:
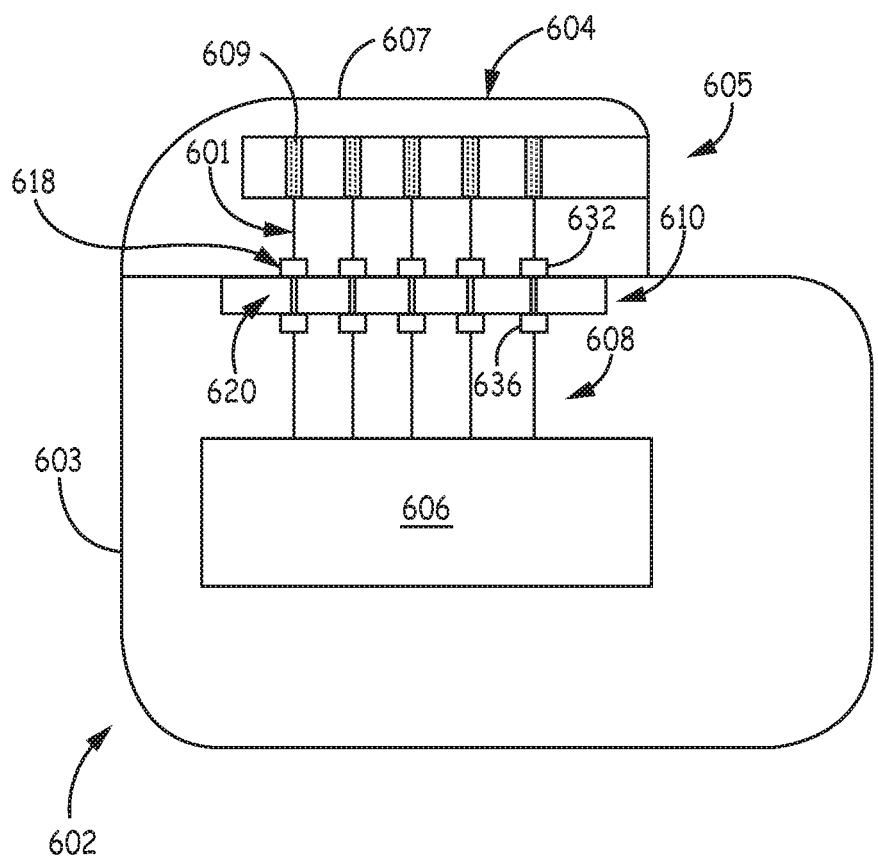
FIG. 11 is a schematic cross-section view of the implantable medical device of the system of FIG. 10.

FIG. 11 is a schematic cross-section view of the IMD 602 of FIG. 10. The IMD 602 further includes a hermetically sealed housing 603 in which electronics 606 are disposed, and the connector header 604 disposed on or attached to the housing. The housing 603 can include any suitable material or combination of materials, e.g., titanium, glass, sapphire, etc. In one or more embodiments, the housing 603 can be electrically conductive to provide a ground electrode for the IMD 602 as is known in the art. A lead receptacle 605 is formed in a housing 607 of the header 604. The receptacle 605 is adapted to receive and electrically couple to contacts 684 of the lead extension 682 (or contacts 692 of the lead 690).

The receptacle 605 has internal contacts 609 positioned to align with and electrically couple with contacts 684 of the lead extension 682 and/or contacts 692 of the lead 690 when the lead extension or lead is properly inserted into the receptacle. The pitch of the internal contacts 609 of FIG. 11 is adapted to allow electrical connection between the contacts 684 of the lead extension 682 or contacts 692 of lead 690.

Electronics 606 are adapted to send electrical signals to a tissue of a patient, or receive signals from a tissue of a patient, through leads operably coupled to the electronics of the IMD 602. As used herein, the term "transmitted electrical signals" is used to refer to both the signals sent by electronics 606 to tissue of the patient or received by the electronics from the tissue of the patient. In one or more embodiments, the feedthrough assembly 610 is electrically coupled to the electronics 606. For example, conductors 608 of IMD 602 can be electrically coupled to internal contacts 609 of lead receptacle 605 via feedthroughs 618 of feedthrough assembly 610, which extend through hermetically sealed housing 603. For example, in one or more embodiments, conductor 608 can be electrically coupled to the electronics 606 and an internal contact 636 of feedthrough 618. The internal contact 636 can be electrically coupled to external contact 632 of the feedthrough assembly 618 through conductive material disposed in a via 620. The external contact 632 can in turn be electrically coupled to the internal contact 609 of lead receptacle 605 by conductor 601. A conductive pathway is, therefore, formed between the internal contact 609 of lead receptacle 605 and electronics 606. Feedthrough assembly 610 can include any feedthrough assembly described herein, e.g., feedthrough assembly 10 of FIGS. 1A-4.

In one or more embodiments, each conductor 608 can electrically couple an internal contact 609 of the lead receptacle 605 to a discrete channel of the electronics 606. As used herein, a "channel" of the electronics is a discrete electronic pathway through which signals may be transmitted independently of another channel. The feedthroughs 618 can be electrically coupled with internal contacts 609 via welding, soldering, brazing, coupling via conductive wires, or the like. Each channel of the electronics 606 can be independently coupled with a discrete internal contact 609 of a receptacle, which can be coupled with a discrete contact 684 of the lead extension 682 or contact 692 of the lead 690, which can be coupled with a discrete electrode 694 of the lead. Accordingly, each channel of the electronics 606 can be operably coupled to a given electrode 694 of a lead.

The feedthrough assembly 610 can be disposed within the header 604 such that the housing 607 surrounds the assembly, and the assembly can be attached to a sidewall of the housing 603 of the IMD 602 between the header and the housing. In one or more embodiments, the feedthrough assembly 610 can be disposed on any sidewall of the housing such that the system does not include a header. The feedthrough assembly 610 can be disposed on a sidewall of the housing 603 using any suitable technique or combination of techniques. In one or more embodiments when a header is not utilized, the feedthrough assembly 610 can be covered with an insulative covering (e.g., silicone).

Figure 12:
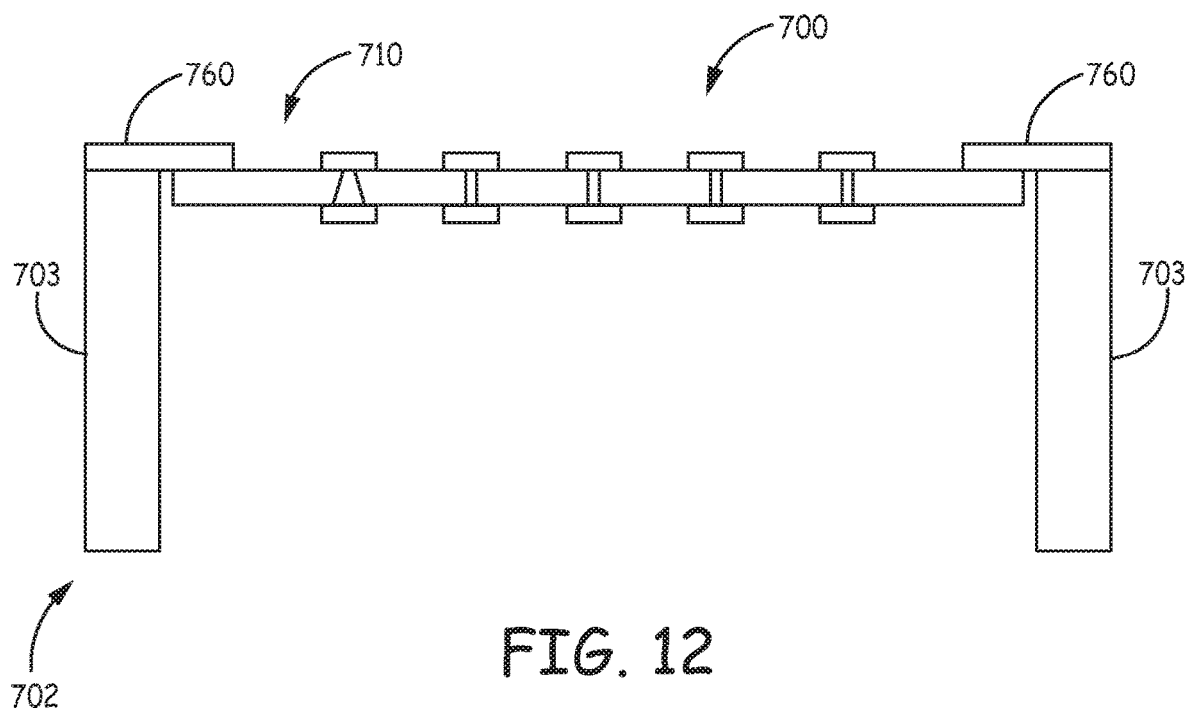
FIG. 12 is a schematic cross-section view of a portion of another embodiment of a hermetically-sealed package that includes a feedthrough assembly.

In general, the various embodiments of feedthrough assemblies described herein can be attached to a housing of a hermetically-sealed package (e.g., an implantable medical device). For example, FIG. 12 is a schematic cross-section view of a portion of one embodiment of a hermetically-sealed package 700. All of the design considerations and possibilities regarding the package 2 of FIGS. 1A-4 apply equally to the package 700 of FIG. 12. As illustrated in FIG. 12, a weld ring 760 of feedthrough assembly 710 can be attached to housing 703 of package 700. Feedthrough assembly 710 can include any feedthrough assembly described herein, e.g., feedthrough assembly 10 of FIGS. 1A-4. Any suitable technique or combination of techniques can be utilized to attach the assembly 710 to the housing 703. In one or more embodiments, the weld ring 760 can be hermetically sealed to the housing 703 by a bond (e.g., laser bond) between the housing and the weld ring. Any suitable technique or combination of techniques described herein can be utilized to form the bond.

Figure 13:
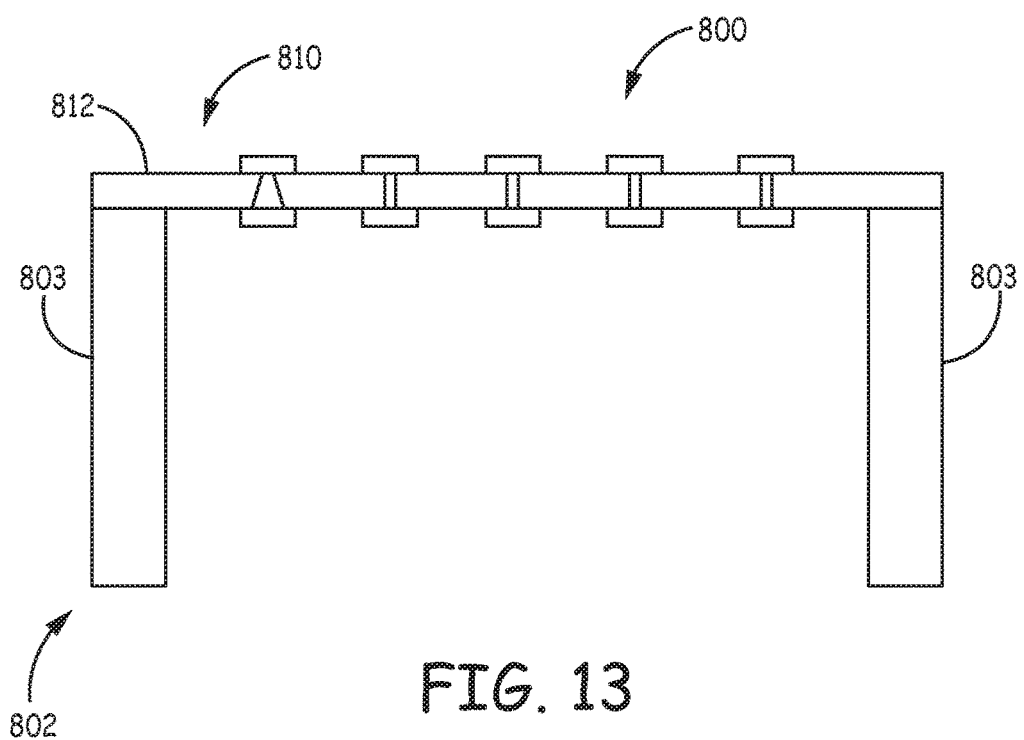
FIG. 13 is a schematic cross-section view of a portion of another embodiment of a hermetically-sealed package that includes a feedthrough assembly.

In one or more embodiments, a feedthrough assembly does not include a weld ring, and a substrate of the assembly can be directly attached to a housing of a hermetically-sealed package. For example, FIG. 13 is a schematic cross-section view of another embodiment of a hermetically-sealed package 800. All of the design considerations and possibilities regarding the package 2 of FIGS. 1A-4 apply equally to the package 800 of FIG. 13. In the illustrated embodiment, feedthrough assembly 810 of package 800 is attached to housing 803 of the package 800 without the use of a weld ring. Feedthrough assembly 810 can include any suitable feedthrough assembly described herein, e.g., feedthrough assembly 10 of FIGS. 1A-4. In one or more embodiments, the housing 803 of the package 800 can be hermetically sealed to substrate 812 of the feedthrough assembly 810 by a bond (e.g., laser bond) between the housing and the substrate 812. The bond can be formed using any suitable technique or combination of techniques described herein. See also the techniques described in co-owned U.S. Pat. No. 8,796,109 to Ruben et al.

Figure 14A:
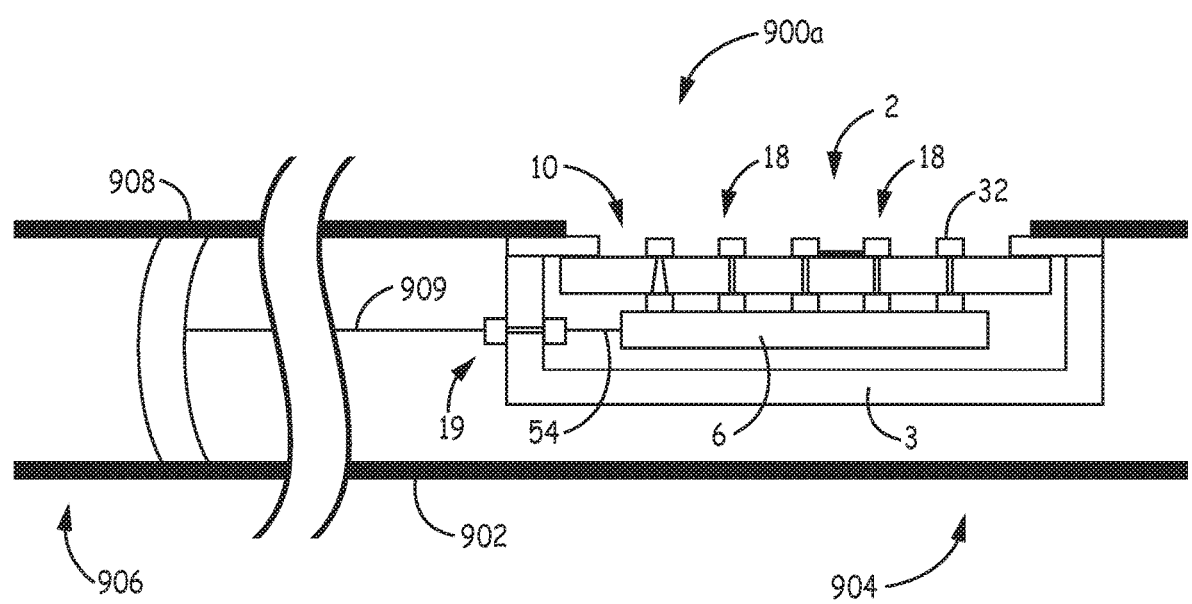
FIG. 14A is a schematic plan view of one embodiment of a lead that includes a hermetically-sealed package.
Figure 14B:
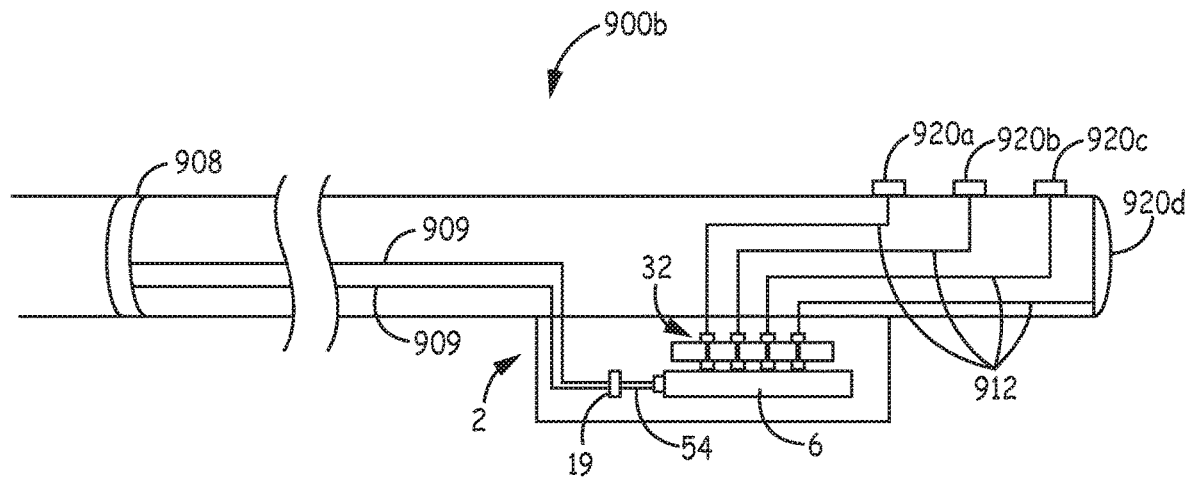
FIG. 14B is a schematic plan view of one embodiment of a lead that includes a hermetically-sealed package.

The various embodiments of hermetically-sealed packages described herein can be utilized with any system or device. For example, FIGS. 14A-B are schematic plan views of embodiments of leads 900a, 900b (collectively, "leads 900"). The leads 900 can be any suitable lead known in the art (e.g., lead 690 of implantable medical device 600 of FIGS. 10-11). All of the design considerations and possibilities regarding lead 690 (and lead extension 682) of FIG. 10 apply equally to lead 900s of FIGS. 14A-B. Further, the leads 900 can be utilized with any suitable external medical device or implantable medical device (e.g., implantable medical device 602 of system 600 of FIGS. 10-11). The leads 900 includes a lead body 902 that has a distal portion 904 and a proximal portion 906 that includes one or more contacts 908.

Referring to FIG. 14A, one difference between lead 900a and lead 690 is that lead 900a includes the hermetically-sealed package 2 of FIGS. 1A-4 disposed in a portion, e.g., the distal portion 904, of the lead body 902. Although the lead 900a is illustrated as including the hermetically-sealed package 2 of FIGS. 1A-4, any hermetically-sealed package can be utilized with the lead.

In one or more embodiments, the discrete contact 908 of the lead 900a can be electrically coupled to the package 2 using any suitable technique or combination of techniques. In one or more embodiments, the discrete contact 908 of the lead 900a can be electrically coupled to the package 2 through one or more conductors or filers 909 that are disposed on or within the lead body 902. The discrete contact 908 can be electrically coupled to one or more of the feedthroughs 18 of the package 2 either directly or through the electronic device 6. For example, in one or more embodiments, the electronic device 6 can be a multiplexer that is electrically coupled to one or more discrete contacts 908 of the lead and the feedthrough assembly 18.

Turning to FIG. 14B, lead 900b depicts hermetically-sealed package 2 of FIGS. 1A-4 that is coupled to a portion, e.g., the distal portion 904, of the lead body 902. For example, the package 2 is coupled to an external portion of lead 900b. As depicted in FIG. 14B, the lead 900b optionally includes one or more output conductors 912 that are coupled to the package 2. The one or more output conductors 912 can electrically couple the package 2 to electrodes 920a-d that are disposed on the lead 900b. In one embodiment, the multiplexer in package 2 can be used for selective coupling of one or more of the electrodes 920a-d to the one or more conductors or filers 909 as will be described in more detail below.

With reference to both FIGS. 14A-B, any suitable multiplexer can be utilized with the leads 900, e.g., the multiplexers described in co-owned U.S. Pat. No. 7,822,482 to Gerber. The multiplexer 6 can be electrically coupled to one or more discrete contacts 908 by a conductor or filer 909 that is disposed on or within the lead body 902 and is electrically coupled to feedthrough 19 as shown in FIGS. 14A-B. The feedthrough 19 can be any suitable feedthrough described herein, e.g., feedthrough 18 of assembly 10. Further, any suitable technique or combination of techniques can be utilized to form the feedthrough 19 through the housing 3 of package 2, e.g., the same techniques described for forming feedthrough 18 of feedthrough assembly 10. The feedthrough 19 can be a part of feedthrough assembly 10 or a discrete feedthrough that is formed separately through the housing 3. In one or more embodiments, the feedthrough 19 can be a component of a second feedthrough assembly that is attached to or forms a part of the housing 3 of package 2. In general, the package 2 can include any suitable number of feedthrough assemblies.

The feedthrough 19 can provide a hermetically-sealed conductive pathway from the discrete contact 908 to the electronic device 6. Although one feedthrough 19 is illustrated as being formed through housing 3 of package 2, any suitable number of feedthroughs can be formed through the housing to electrically couple any suitable number of contacts 908 to the electronic device 6.

The lead body 902 can include one or more conductors 909 that provide one or more inputs to the multiplexer 6. And the package 2 can include one or more conductors that provide one or more outputs from the multiplexer 6 to the one or more feedthroughs 18. In one or more embodiments, outputs of the multiplexer can be directly coupled to one or more internal contacts 36 of the feedthrough assembly 10. In one or more embodiments, the number of outputs of the multiplexer 6 corresponds to the number of external contacts 32, as there is one output for each external contact. Further, in one or more embodiments, the number of outputs is greater than the number of input conductors 909. The use of multiplexer 6 within lead body 902 can reduce the number of input conductors 909 that extend along the entire length of the lead body.

With the multiplexer 6 placed in the distal portion 904 of the leads 900, the number of input conductors 909 that extend along substantially the entire length of lead body 902 can be reduced. For example, the input conductors 909 may include a chip power conductor, a chip ground conductor, a serial addressing conductor, a stimulation power conductor, and a stimulation return conductor return. The chip power and chip ground conductors can deliver operating power to the multiplexer 6. The stimulation power and return conductors deliver stimulation pulses for application across a set of electrodes (e.g., electrodes 920a-d) in distal portion 904 of the leads 900, which, in the illustrated embodiment, are the external contacts 32 of the feedthrough assembly 10. The serial addressing conductor carries a serial codeword that identifies a combination of electrodes for application of stimulation pulses. Each of the electrodes 920a-d can be electrically coupled to the external contacts 32 directly or through one or more output conductors 912 as shown in FIG. 14B. In response to the codeword, the multiplexer 6 configures a switch matrix to direct the stimulation pulses across the specified combination of two or more electrodes. The codeword may be transmitted by pulse width modulation or other serial bus schemes, and may specify the electrodes to be included in an electrode combination, as well as the polarities of the electrodes. In response to the address codeword, multiplexer 6 applies the stimulation current across the specified set of electrodes.

In one or more embodiments, one or more therapeutic electrodes can be electrically coupled to one or more external contacts 32 of the feedthrough assembly 10. In one or more embodiments, one or more of the external contacts 32 can be coupled to electrodes through conductors to provide electrical stimulation therapy to a patient or sense physiological signals, such as cardiac signals, from a patient.

As previously stated herein, the external contacts 32 can be disposed in any suitable arrangement. In one or more embodiments, the external contacts 32 can be disposed in a two-dimensional arrangement such as an array (e.g., array 230 of FIG. 6), or a three-dimensional arrangement. In other words, the feedthrough assembly 10 can include a substrate having a three-dimensional shape, e.g., spherical, cubic, conical, etc. In such embodiments, one or more feedthroughs 18 can be disposed in any arrangement such that the external contacts 32 can be provided in a three-dimensional configuration. See, e.g., co-owned U.S. Pat. No. 7,822,482 to Gerber.

Figure 16A:
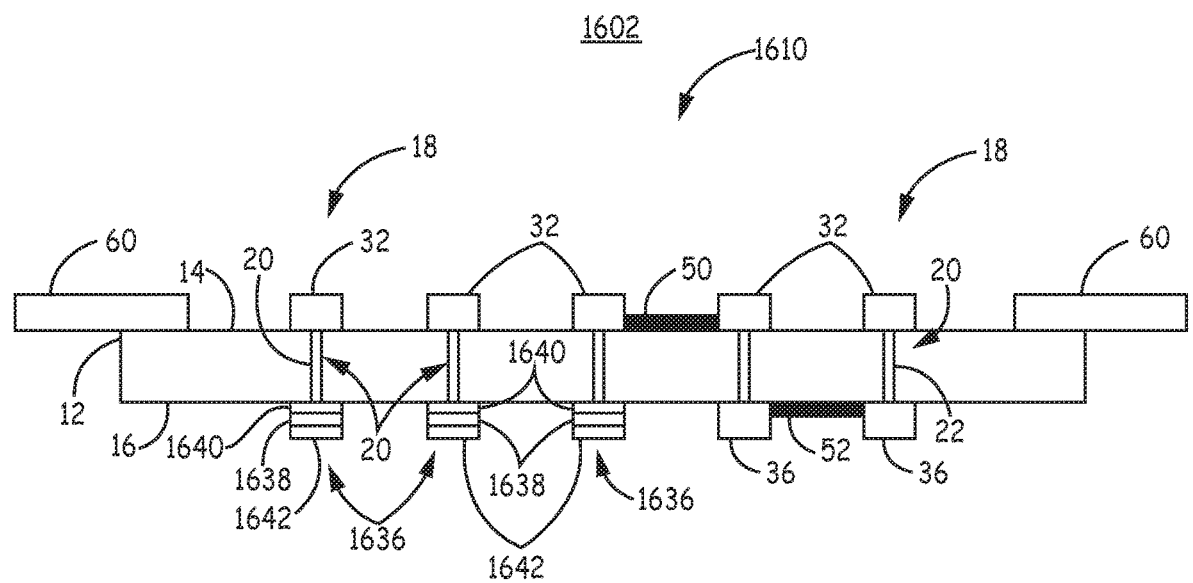
FIG. 16A is a schematic cross-section view of embodiments of hermetically-sealed packages that include a feedthrough assembly.
Figure 16B:
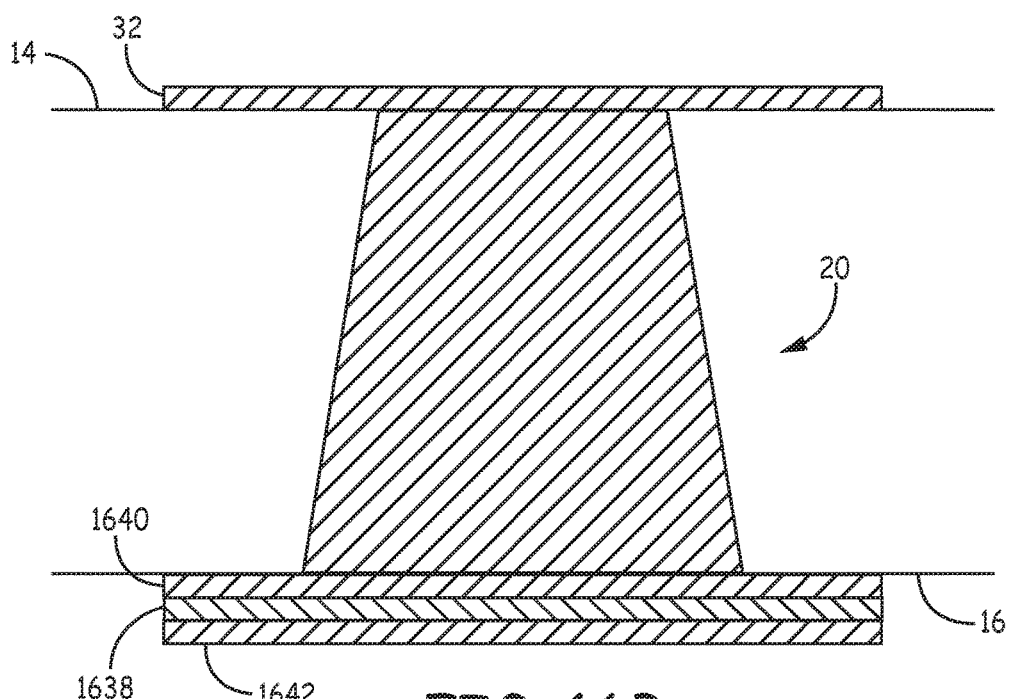
FIG. 16B is a magnified schematic cross-section view of an embodiment of hermetically-sealed packages that include a feedthrough assembly.

FIGS. 16A-B depict another alternative embodiment of a feedthrough assembly 1610. For ease of discussion, the elements that are common to FIGS. 1A & 1B and FIGS. 16A-B are numbered with identical reference designators. All of the design considerations and possibilities regarding the feedthrough assembly 10 of FIGS. 1A-4 apply equally to the feedthrough assembly 1610 of FIGS. 16A-B. Assembly 1610 includes feedthroughs 18. Each feedthrough 18 includes an external contact 32 that can be electrically coupled to an internal contact, conductor, or device. For example, the external contact 32 can be electrically coupled to internal contact 36 as described with reference to FIGS. 1A-4.

As those skilled in the art can appreciate, the assembly 1610 can be electrically coupled to any suitable device or devices that are external to the package 1602. For example, in one or more embodiments, the package 1602 can be electrically coupled to a lead of an implantable medical device. In some situations, such lead wires effectively act as an antenna and thus tend to collect stray or electromagnetic interference (EMI) signals for transmission to the interior of the package 1602 and onto electronic components and circuitry that are electrically coupled thereto. Such EMI signals may interfere with the proper operation of the electronic components and circuitry.

To mitigate the deleterious effect of the EMI signals, one or more of the external contacts 32 can optionally be coupled to a capacitor 1636. The capacitor 1636 shunts any EMI signals from the exterior of the assembly 1610. In particular, the capacitor 1636 is coupled to via 20 to suppress and/or prevent transfer of such EMI signals from the outer surface 14 to the interior of the assembly 1610 through the conductive pathway defined by the via 20. In operation, the capacitor 1636 permits passage of relatively low frequency electrical signals from the exterior of the assembly 1610, while shunting and shielding undesired interference signals of typically high frequency to the components that are coupled to the capacitor 1636 in the interior of the assembly 1610.

The capacitor 1636 includes an insulator 1638 that is disposed between a first conductor 1640 and a second conductor 1642. The first conductor 1640 may be formed utilizing any suitable technique such as the techniques described with reference to the contact 36, including but not limited to copper, titanium, aluminum, chromium, nickel, gold, composites (e.g., silver-filled epoxies), and combinations thereof. First conductor 1640 can include any suitable material or combination materials, e.g., any of the conductive materials described herein, such as the same materials utilized for contact 36. Insulator 1638 is formed from any suitable dielectric material such as silicon dioxide, silicon nitride, tantalum pentoxide, or barium strontium titanate. These may be formed using standard thin film techniques such a chemical vapor deposition, atomic layer deposition, printing, dispensing or laminating. A second conductor 1642 is formed on the insulator 1638, through for example, internal metallization of one or more conductive material(s) directly onto the non-conductive material of insulator 1638. The materials selection for the second conductor 1642 can include one or more of the materials used to form the conductor 36, including but not limited to copper, titanium, aluminum, chromium, nickel, gold, composites (e.g., silver-filled epoxies), and combinations thereof. It should be noted that the depiction of the capacitor 1636 as being a two plate capacitor is solely provided for ease of description and is not intended to be limited as such. Rather, it is contemplated the disclosure can be extended to applications where the capacitors 1636 include any number of plates, such as two or more plates, depending on the desired capacitance for any given implementation.

Figure 17A:
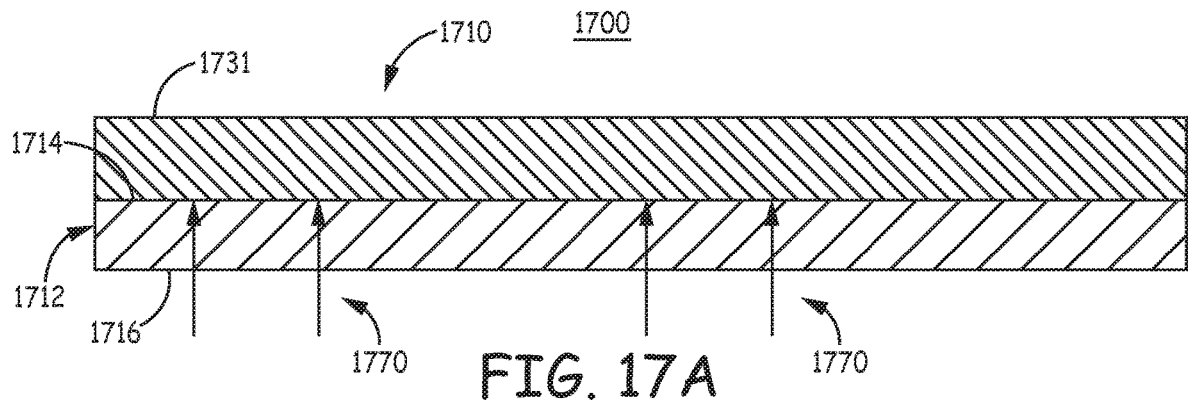
FIG. 17A is a schematic cross-section view of another embodiment of a method of forming a feedthrough assembly.

FIGS. 17A-E are schematic cross-section views of another embodiment of a method 1700 for forming a feedthrough assembly 1710. All of the design considerations and possibilities regarding the feedthrough assembly 10 of FIGS. 1A-4, feedthrough assembly 310 of FIGS. 7A-E, feedthrough assembly 410 of FIGS. 8A-E, feedthrough assembly 510 of FIGS. 9A-E, and feedthrough assembly 1610 of FIGS. 16A-B apply equally to the feedthrough assembly 1710 of FIGS. 17A-E. In method 1700, a conductive material layer 1731 can be disposed on and/or coupled to an outer surface 1714 of a substrate 1712. The conductive material layer 1731 can comprise a conductive sheet or foil. The conductive material layer 1731 can be attached to the outer surface 1714 of the substrate 1712 using any suitable technique or combination of techniques, e.g., forming a bond that hermetically seals the conductive layer to the outer surface. For example, as illustrated in FIG. 17A, electromagnetic radiation 1770 is directed through inner surface 1716 of the substrate 1712 and directed at an interface of the conductive material layer 1731 and the outer surface 1714 to form one or more bonds between the conductive material layer 1731 and the outer surface.

Figure 17B:
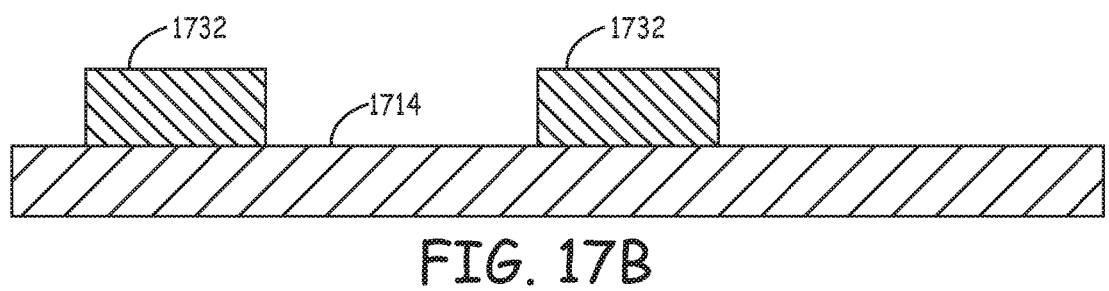
FIG. 17B is a schematic cross-section view of another embodiment of a method of forming a feedthrough assembly.

One or more portions of the conductive material layer 1631 can be removed to form one or more external contacts 1632 on the outer surface 1614 of the substrate 1612 as shown in FIG. 17B. Any suitable technique or combination of techniques can be utilized to form the external contacts 1632 including, for example, photolithography, etching, laser ablation, etc. In some embodiments, a mask or masks can be formed on the outer surface 1614 of the substrate, and the conductive material layer 1631 can be formed over the mask. Portions of the conductive material layer 1631 that are formed on the mask itself can be removed using any suitable technique or combination of techniques to form external contacts 1632. In one or more embodiments, the bond formed when the conductive material layer 1631 was attached to the substrate 1612 remains between the external contact 1632 and the outer surface 1614 of the substrate 1612 such that the contact is hermetically sealed to the outer surface. Any suitable technique or combination of techniques can be utilized to form external contacts 1632.

Figure 17C:
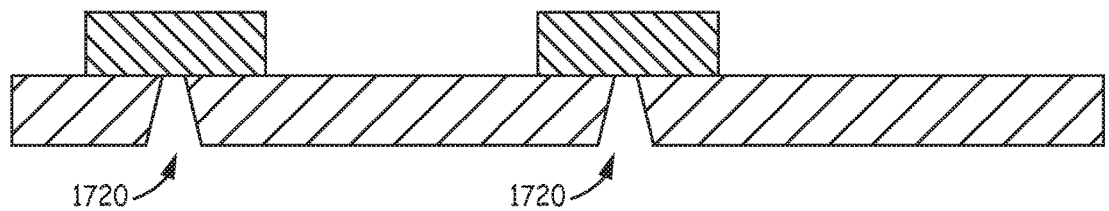
FIG. 17C is a schematic cross-section view of another embodiment of a method of forming a feedthrough assembly.

As shown in FIG. 17C, one or more vias 1720 can be formed through the substrate 1712. The via 1720 can be formed such that it is within a closed shape or region defined by the bond such that the bond surrounds the via. Because the via 1720 is within the shapes or regions formed by the bonds, the via 1720 can be protected from the external environment. In one or more embodiments, an etch stop layer can be formed between the conductive material layer 1731 and the outer surface 1714 of the substrate 1712 to prevent the formation of the via 1720 from removing portions of the external contact 1732.

Figure 17D:
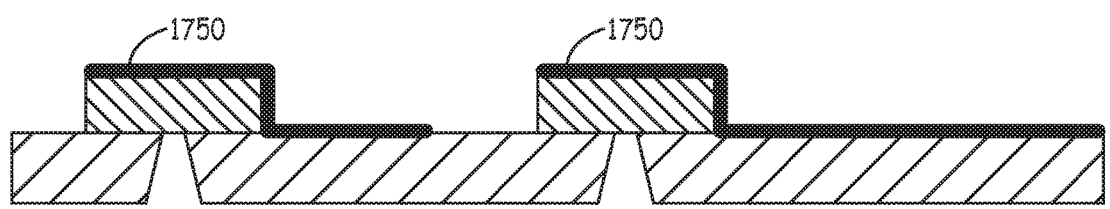
FIG. 17D is a schematic cross-section view of another embodiment of a method of forming a feedthrough assembly.

One or more conductors 1750 can optionally be formed on the external contact 1732 and/or on the outer surface 1714 of the substrate 1712 as shown in FIG. 17D. In one or more embodiments, one or more conductors 1750 can be electrically coupled to the external contact 1732. Any suitable technique or combination of techniques can be utilized to form conductors 1750. In one or more embodiments, the conductors 1750 can be provided by forming a conductive material layer over the external contact 1732 and the outer surface 1714. This conductive material layer can then be patterned to form conductor 1750 in any desirable configuration.

Figure 17E:
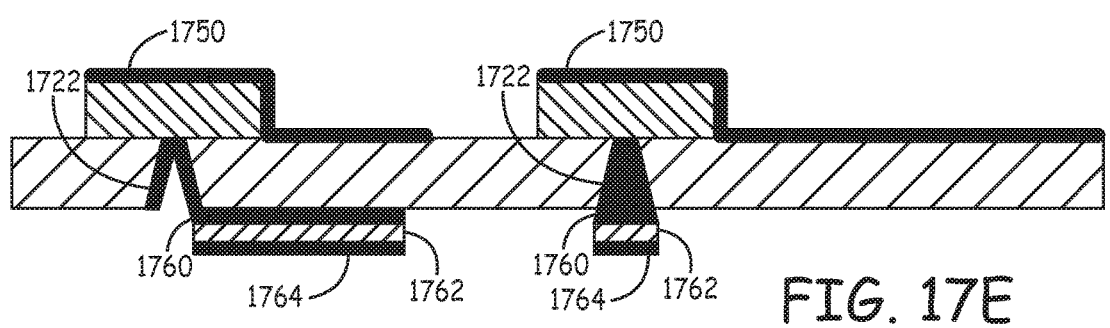
FIG. 17E is a schematic cross-section view of another embodiment of a method of forming a feedthrough assembly.

As shown in FIG. 17E, conductive material 1722 can be disposed in the via 1720 to provide a conductive pathway from the external contact 1732 to conductors, contacts, electronic devices, etc. disposed on the inner-surface side of the substrate 1712. Any suitable technique or combination of techniques can be utilized to form the conductive material 1722 in the via 1720. As mentioned herein, the via 1720 can be substantially filled with the conductive material 1722. In one or more embodiments, the conductive material 1722 can be disposed on a portion or portions of one or more sidewalls of the vias as shown in FIG. 17E.

Further, one or more EMI filtering capacitors can optionally be formed on the inner surface 1716 of the substrate 1712. Accordingly, one or more first conductors 1760, corresponding to the number of desired capacitors, can be formed either simultaneously with forming conductive material in the vias or sequentially. In one or more embodiments, the same material utilized for the conductive material 1722 can also be utilized to form first conductors 1760. First conductors 1760 can be formed using any suitable technique or combination of techniques. Subsequently, insulator 1762 is coupled to the first conductor 1760 using any suitable techniques, such as chemical vapor deposition, plasma vapor deposition, physical vapor deposition. The same techniques may similarly be utilized to couple a second conductor 1764 to the insulator 1762. As such, the first and second conductors 1760, 1764 and the insulator 1762 define a capacitor structure that is formed on the inner surface 1716 of substrate 1712.

All headings provided herein are for the convenience of the reader and should not be used to limit the meaning of any text that follows the heading, unless so specified.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements.

The words "preferred" and "preferably" refer to embodiments of the disclosure that may afford certain benefits, under certain circumstances; however, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a," "an," and "the" are not intended to refer to only a singular entity, but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise. The use of the term "and/or" in certain portions of this disclosure is not intended to mean that the use of "or" in other portions cannot mean "and/or."

The term "and/or" means one or all of the listed elements or a combination of any two or more of the listed elements.

As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

All references and publications cited herein are expressly incorporated herein by reference in their entirety into this disclosure, except to the extent they may directly contradict this disclosure. Illustrative embodiments of this disclosure are discussed and reference has been made to possible variations within the scope of this disclosure. These and other variations and modifications in the disclosure will be apparent to those skilled in the art without departing from the scope of the disclosure, and it should be understood that this disclosure is not limited to the illustrative embodiments set forth herein. Accordingly, the disclosure is to be limited only by the claims provided below.

What is claimed is:

1. A method comprising:
    forming a feedthrough assembly comprising a non-conductive substrate that comprises an outer surface and an inner surface;
    attaching a conductive weld ring to the outer surface of the non-conductive substrate by directing laser light through the non-conductive substrate from the inner surface of the non-conductive substrate to an interface of the weld ring and the outer surface of the non-conductive substrate to form a bond; and attaching the weld ring to a housing by forming a laser bond disposed between the weld ring and the housing that hermetically seals electronic devices and circuitry disposed within an enclosure formed by the weld ring and the housing.

2. The method of claim 1, wherein forming the feedthrough assembly comprises forming a feedthrough, wherein forming the feedthrough comprises:

forming a via through the non-conductive substrate;

forming a conductive material in the via;

forming an external contact over the via, wherein the external contact is electrically coupled to the conductive material formed in the via; and attaching the external contact to the outer surface of the non-conductive substrate by forming a laser bond that surrounds the via and hermetically seals the external contact to the outer surface of the non-conductive substrate, wherein the laser bond is disposed between the external contact and the outer surface of the non-conductive substrate, and further wherein the laser bond is in contact with the external contact and the outer surface of the non-conductive substrate.

3. The method of claim 2, wherein the weld ring surrounds the feedthrough of the feedthrough assembly.

4. The method of claim 2, wherein forming the feedthrough assembly further comprises forming a conductor on the outer surface of the non-conductive substrate, wherein the external contact is electrically coupled to the conductor.

5. The method of claim 2, further comprising disposing an electronic device on the inner surface of the non-conductive substrate, wherein the electronic device is electrically coupled to the conductive material in the via of the feedthrough, and wherein the electronic device is attached to the non-conductive substrate by a bond.

6. The method of claim 5, wherein the electronic device is disposed within the housing when the housing is hermetically sealed to the feedthrough assembly.

7. The method of claim 1, wherein the bond that attaches the conductive weld ring to the outer surface of the non-conductive substrate is formed adjacent to a perimeter of the non-conductive substrate between the non-conductive substrate and the weld ring.

8. The method of claim 7, wherein the bond comprises a laser bond.

9. The method of claim 8, wherein the laser bond comprises a bond line.

10. The method of claim 1, wherein the weld ring is hermetically sealed to the non-conductive substrate.

11. The method of claim 1, further comprising electrically connecting the weld ring to a ground terminal disposed on the housing.

12. The method of claim 1, wherein the feedthrough assembly further comprises an internal contact disposed over the via of the feedthrough assembly on the inner surface of the non-conductive substrate, wherein the internal contact is electrically coupled to the conductive material in the via.

13. The method of claim 12, further comprising electrically connecting the weld ring to the internal contact.

14. The method of claim 13, wherein the weld ring is electrically connected to the internal contact by a second via disposed through the non-conductive substrate.

15. The method of claim 1, wherein the weld ring comprises at least one of copper, silver, titanium, niobium, zirconium, tantalum, stainless steel, platinum, or iridium.

16. The method of claim 1, further comprising disposing an interfacial layer between the weld ring and the outer surface of the non-conductive substrate.

17. The method of claim 16, wherein the interfacial layer comprises a thickness of no greater than 10 μm.

18. The method of claim 1, further comprising electrically coupling a lead to the external contact.

19. The method of claim 1, wherein the non-conductive substrate comprises transparent material that is substantially transmissive to a transmitted light having a pre-determined magnitude such that the energy transmitted through the substantially transmissive substrate is at least one of: sufficient to activate the bonding process at the interface via absorption by opaque material of the weld ring, or absorbable by the transparent material of the substrate without melting, distorting, or otherwise modifying the bulk properties of the transparent material away from the interface.

20. The method of claim 2, wherein the laser bond that attaches the external contact to the outer surface of the non-conductive substrate comprises a bond line.

* * * * *